US007919685B2

(12) United States Patent
Ursin et al.

(10) Patent No.: US 7,919,685 B2
(45) Date of Patent: Apr. 5, 2011

(54) FATTY ACID DESATURASES FROM TETRASELMIS SUECICA

(75) Inventors: Virginia Ursin, Pawcatuck, CT (US); Byron Froman, Davis, CA (US); Henry E. Valentin, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 759 days.

(21) Appl. No.: 11/779,761

(22) Filed: Jul. 18, 2007

(65) Prior Publication Data

US 2008/0020122 A1 Jan. 24, 2008

Related U.S. Application Data

(60) Provisional application No. 60/831,838, filed on Jul. 19, 2006.

(51) Int. Cl.
*A01H 5/00* (2006.01)
*C12N 15/82* (2006.01)
*C07H 21/04* (2006.01)
*C12N 5/10* (2006.01)
*A23K 1/00* (2006.01)

(52) U.S. Cl. ....... 800/298; 800/281; 536/23.2; 435/410; 426/615

(58) Field of Classification Search .................. None
See application file for complete search history.

(56) References Cited

U.S. PATENT DOCUMENTS

| | | | |
|---|---|---|---|
| 4,910,141 A | 3/1990 | Wong et al. | 536/23.1 |
| 5,057,419 A | 10/1991 | Martin et al. | 435/134 |
| 5,097,093 A | 3/1992 | Vanderventer et al. | 800/200 |
| 5,349,123 A | 9/1994 | Shewmaker et al. | 800/205 |
| 5,376,541 A | 12/1994 | Kawashima et al. | 435/36 |
| 5,405,765 A | 4/1995 | Vasil et al. | 435/172.3 |
| 5,443,974 A | 8/1995 | Hitz et al. | 435/172.3 |
| 5,484,956 A | 1/1996 | Lundquist | 800/205 |
| 5,498,830 A | 3/1996 | Barry et al. | 800/205 |
| 5,552,306 A | 9/1996 | Thomas et al. | 435/134 |
| 5,591,616 A | 1/1997 | Hiei et al. | 435/172.3 |
| 5,614,393 A | 3/1997 | Thomas et al. | 435/134 |
| 5,614,400 A | 3/1997 | Cahoon et al. | 435/172.3 |
| 5,668,292 A | 9/1997 | Somerville et al. | 800/205 |
| 5,880,275 A | 3/1999 | Fischhoff et al. | 536/23.71 |
| 5,886,244 A | 3/1999 | Tomes et al. | 800/205 |
| 5,952,544 A | 9/1999 | Browse et al. | 800/295 |
| 5,968,809 A | 10/1999 | Knutzon et al. | 435/254.2 |
| 5,972,664 A | 10/1999 | Knutzon et al. | 435/136 |
| 6,051,754 A | 4/2000 | Knutzon | 800/281 |
| 6,075,183 A | 6/2000 | Knutzon | 800/281 |
| 6,117,677 A | 9/2000 | Thompson et al. | 435/410 |
| 6,136,574 A | 10/2000 | Knutzon et al. | 435/134 |
| 6,319,698 B1 | 11/2001 | Barclay | 435/134 |
| 6,355,861 B1 | 3/2002 | Thomas | 800/281 |
| 6,384,301 B1 | 5/2002 | Martinell et al. | 800/294 |
| 6,451,567 B1 | 9/2002 | Barclay | 435/134 |
| 6,459,018 B1 | 10/2002 | Knutzon | 800/320.3 |
| 6,603,061 B1 | 8/2003 | Armstrong et al. | 800/294 |
| 6,803,499 B1 | 10/2004 | Anderson et al. | 800/281 |
| 7,037,692 B1 | 5/2006 | Thompson et al. | |
| 7,622,632 B2 | 11/2009 | Ursin et al. | |
| 7,705,215 B1 | 4/2010 | Adams et al. | |
| 2005/0132441 A1 | 6/2005 | Damude et al. | 800/281 |
| 2005/0132442 A1 | 6/2005 | Yadav et al. | 800/281 |
| 2006/0156435 A1 | 7/2006 | Ursin et al. | |
| 2008/0063691 A1 | 3/2008 | Ursin et al. | |
| 2008/0260929 A1 | 10/2008 | Ursin et al. | |
| 2010/0212045 A1 | 8/2010 | Ursin et al. | |

FOREIGN PATENT DOCUMENTS

| | | |
|---|---|---|
| EP | 0 537 178 | 8/1994 |
| EP | 0 550 162 | 3/2001 |
| EP | 0 644 263 | 12/2002 |
| EP | 0 561 569 | 6/2003 |
| EP | 0 616 644 | 7/2003 |
| EP | 0 736 598 | 8/2004 |
| WO | WO 91/13972 | 9/1991 |
| WO | WO 93/06712 | 4/1993 |
| WO | WO 93/11245 | 6/1993 |
| WO | WO 94/11516 | 5/1994 |
| WO | WO 94/18337 | 8/1994 |
| WO | WO 96/10086 | 4/1996 |
| WO | WO 96/21022 | 7/1996 |
| WO | WO 97/21340 | 6/1997 |
| WO | WO 97/30582 | 8/1997 |
| WO | WO 97/46219 | 12/1997 |
| WO | WO 97/46220 | 12/1997 |
| WO | WO 98/45460 | 10/1998 |
| WO | WO 98/46763 | 10/1998 |
| WO | WO 99/64614 | 12/1999 |
| WO | WO 02/081668 | 10/2002 |

(Continued)

OTHER PUBLICATIONS

Broun et al, Science 282: 1315-1317, Nov. 13, 1998.*
Van de Loo et al, PNAS, USA 92:6743-6747, Jul. 1995.*
Doerks et al, TIG 14(6):248-250, Jun. 1998.*
Brenner, S.E., TIG 15(4): 132-133, Apr. 1999.*
Bork et al, TIG 12(10):425-427, Oct. 1996.*
Traitler et al., "Fractionation of blackcurrant seed oil," *JAOCS*, 65(5):755-760, 1988.
U.S. Appl. No. 08/113,561, filed Aug. 25, 1993, Adams.
"Exciting prospects for stearidonic acid seed oils," *Lipid Technology*, Nov. 1996.
Alonso and Garcia-Maroto, "Plants as 'chemical factories' for the production of polyunsaturated fatty acids," *Biotechnology Advances*, 18(6):481-497, 2000.

(Continued)

*Primary Examiner* — Elizabeth F McElwain
(74) *Attorney, Agent, or Firm* — Byron V. Olsen, Esq.; SNR Denton US LLP

(57) ABSTRACT

The invention relates generally to methods and compositions concerning desaturase enzymes that modulate the number and location of double bonds in long chain poly-unsaturated fatty acids (LC-PUFA's). In particular, the invention relates to methods and compositions for improving omega-3 fatty acid profiles in plant products and parts using desaturase enzymes and nucleic acids encoding for such enzymes. In particular embodiments, the desaturase enzymes are *Tetraselmis suecica* delta 6 desaturases. Also provided are improved soybean oil compositions having GLA and SDA.

19 Claims, 7 Drawing Sheets

FOREIGN PATENT DOCUMENTS

| WO | WO 02/092073 | 11/2002 |
|---|---|---|
| WO | WO 03/075670 | 3/2003 |
| WO | WO 03/072784 | 9/2003 |
| WO | WO 03/099216 | 12/2003 |
| WO | WO 2005/021761 | 3/2005 |
| WO | WO 2005/118814 | 12/2005 |

OTHER PUBLICATIONS

Arondel et al., "Map-based cloning of a gene controlling omega-3 fatty acid desaturation in arabidopsis," *Science*, 258:1353-1355, 1992, Abstract only.

Casas et al., "Transgenic sorghum plants via microprojectile bombardment," *Proc. Natl. Acad. Sci. USA*, 90:11212-11216, 1993.

Conti et al., "γ-linolenic acid production by solid-state fermentation of mucorales strains on cereals," *Bioresource Technology*, 76:283-286, 2001.

Covello et al., "Functional expression of the extraplastidial arabidopsis thaliana oleate desaturase gene (FAD2) in *Saccharomyces cerevisiae*," *Plant Physiology*, 111:223-226, 1996.

EBI Accession No. AEE85555 dated Feb. 23, 2006.

EBI Accession No. AEE85556 dated Feb. 23, 2006.

Fox et al., "Stearoyl-acyl carrier protein delta$^9$ desaturase from ricinus communis is a diiron-oxo protein," *Proc. Natl. Acad. Sci.*, 90:2486-2490, 1993.

Garcia-Maroto et al, "Cloning and molecular characterization of the delta6-desaturase from two echium plant species: production of GLA by heterologous expression in yeast and tobacco," *Lipids*, 37(4):417-26, 2002.

GenBank Accession No. AX577009 dated Jan. 8, 2003.

GenBank Accession No. AY234125, dated May 4, 2003.

GenPept Accession No. AAF08685 dated Nov. 18, 1999.

Horrobin, "Fatty acid metabolism in health and disease: the role of delta-6-desaturase[1]," *Am. J. Clin. Nutr.*, 57(Supp.):732S-737S, 1993.

James and Cleland, "Dietary n-3 fatty acids and therapy for reumatoid arthritis," *Semin Arthritis Rheum*, 27(2):85-97, 1997.

Kossmann et al., In: Carbohydrate Bioengineering, "Transgenic plants as a tool to understand starch biosynthesis," Petersen et al. (Eds.), Elsevier Science B.V.; Amsterdam, 1995.

Libisch et al., "Chimeras of Delta6-fatty acid and Delta8-sphingolipid desaturases,"*Biochem Biophys Res Commun*, 279(3):779-85, 2000.

McDonough et al., "Specificity of unsaturated fatty acid-regulated expression of the *Saccharomyces cerevisiae* OLE1 gene," *J. of Biological Chemistry*, 267(9):5931-5936, 1992.

Meesapyodsuk et al., "Characterization of the regiochemistry and cryptoregiochemistry of a *Caenorhabditis elegans* fatty acid desaturase (FAT-1) expressed in *Saccharomyces cerevisiae*," *Biochemistry*, 39(39):11948-54, 2000.

Michaelson et al., "Functional identification of a fatty acid delta5 desaturase gene from *Caenorhabditis elegans*," *FEBS Lett*, 439(3):215-8, 1998.

Michaelson et al., "Isolation and characterization of a cDNA encoding a Delta8 sphingolipid desaturase from *Aquilegia vulgaris*," *Biochem Soc Trans*, 30(Pt 6):1073-5, 2002.

Napier et al., "A new class of cytochrome b5 fusion proteins," *Biochem J*, 328:717-720, 1997.

Napier et al., "Identification of a *Caenorhabditis elegans* Delta6-fatty-acid-desaturase by heterologous expression in *Saccharomyces cerevisiae*," *Biochem J*, 330(Pt 2):611-4, 1998.

Napier et al., "The role of cytochrome b5 fusion desaturases in the synthesis of polyunsaturated fatty acids," *Prostaglandins Leukot Essent Fatty Acids*, 68(2):135-43, 2003.

Post-Beittenmiller et al., "Expression of holo and Apo forms of spinach acyl carrier protein-I in leaves of transgenic tobacco plants," *The Plant Cell*, 1:889-899, 1989.

Reddy et al., "Expression of a cyanobacterial delta$^6$-desaturase gene results in γ-linolenic acid production in transgenic plants," *Nature Biotechnology*, 14:639-642, 1996.

Reddy et al., "Isolation of a delta 6-desaturase gene from the cyanobacterium *synechocystis* sp. strain PCC 6803 by gain-of-function expression *anabaena* sp. strain PCC 7120," *Plant Mol. Biol.*, 22(2):293-300, 1993, Abstract only.

Sayanova et al., "Histidine-41 of the cytochrome b5 domain of the borage delta6 fatty acid desaturase is essential for enzyme activity," *Plant Physiol*, 121:641-646, 1999.

Sayanova et al., "Identification of primula fatty acid delta 6-desaturases with n-3 substrate preferences," *FEBS Letters*, 542:100-104, 2003.

Sayanova et al., "$\Delta^6$-unsaturated fatty acids in the species and tissues of the primulaceae," *Phytochemistry*, 52:419-422, 1999.

Shanklin et al., "Eight histidine residues are catalytically essential in a membrane-associated iron enzyme, stearoyl-CoA desaturase, and are conserved in alkane hydroxylase and xylene monooxygenase," *Biochemistry*, 33:12787-12794, 1994.

Sperling and Heinz, "Desaturases fused to their electron donor," *Eur J Lipid Sci Technolo*, 103:158-180, 2001.

Sperling et al., "Functional identification of a delta8-sphingolipid desaturase from *Borago officinalis*," *Arch Biochem Biophys*, 388(2):293-8, 2001.

Stephanopoulos et al., "Metabolic engineering—methodologies and future prospects," *Trends in Biotechnology*, 11:392-396. 1993.

Whitney et al., "Functional characterisation of two cytochrome b5-fusion desaturases from *Anemone leveillei*: the unexpected identification of a fatty acid Delta6-desaturase," *Planta*, 217(6):983-92, 2003.

* cited by examiner

SEQUENCE LISTING

```
<160> NUMBER OF SEQ ID NOS: 24

<210> SEQ ID NO 1
<211> LENGTH: 1533
<212> TYPE: DNA
<213> ORGANISM: Tetraselmis suecica

<400> SEQUENCE: 1
atgggcaggg gtgggtttac tgatacgccg atgcggggtg gggcggaggg ggaagaagtc      60
cttctgaaga ctaaggcggg cgacgtgggt tttctgagga ccgtcctccg cgtggtgctc     120
gacttcaaca actcggcggc cgagaaccgc gcggagtact ataaagtgaa gaaggcggcg     180
gatgaagcga aggcagctgc gggcgagcgt cgtcgcacca gccgcgccaa actggaacag     240
aagacgagta aagtgagccg tgcggaggta gcggaacaca acgatgtgca cgactgctgg     300
atggtcatca aagggaaggt ctacgacgtg accgactttg cggcgacgca tcccggcggc     360
cgagtgatct acacctacgc ggggaaggac gccaccgacg tgtttgcggc cttccatgcc     420
ggaggcacct ggtcgcaact gtcggagctg caggtgggcg agctggccga ggaggatgcc     480
accaagcccg aggaccccat cgtgcaagat ttccgcaacc tgcgagcaaa gatggttgca     540
gagggtttgt tcaagtcaga caagctgtac tacgtgtaca agaccctatc cactctgtcc     600
attgcgctgc tggcgtatgg ggcgctgtct gcgtggggta gttccctgcc gggcatactc     660
ttctctgctt tcttgcttgg cctcttttgg cagcagtgcg gctggctcgc gcatgatttc     720
tgtcacaacc aggtgtttcg caatcggaca tacaacacat ggggtggctt ccttgtgggc     780
tctgtgtggg gcgggttcag tgtggactgg tggaagggga agcacaacac ccaccatgct     840
gcccccaatg agatcacggc cggtggcatg cctgtggacc agacatcga cacgctgccc     900 ctgatcgcat ggagccctga gctgctatcc aacgtgcacg acgccgccta ccgcgccttc     960
atccgtctcc agcactacct cttcttcccc atcctctgct ttgcccgtat gagctgggct    1020
cagcagagcg ccacgcaccc cttcgacgcc atcaagcaca ccgccaacgt tcagccccgc    1080
gttgagaagc tgtccattgc gctgcactat ggctggctac tcctctttgc cttcagccag    1140
ctccctctcc tccgcggcgt cggcttcctg ctcgccagcc agatgatgtc agggataatg    1200
ctcagcctgg tgttcgtgca gagccacaac gggatggaga tttaccacga gcccaaggat    1260
ttcttcacgg cgcagctcgt ctccacgcgc aacatattcg gtgcgttgag tgaccgagtc    1320
tacggcccct tcaacgattg gttcacgggt ggcctcaact atcagatcga gcatcacctc    1380
ttcccgacca tgcctcgcca ccgcctctcc aaggcgcagg tccacgtgat ggaggtgtgc    1440
aagaagcacg ggttggtgta tgagaactgc agcatgacag agggaacggt gcgggtgctc    1500
agcgcactgg cggacatcgc ggcacttgct tag                                 1533
```

```
<210> SEQ ID NO 2
<211> LENGTH: 510
<212> TYPE: PRT
<213> ORGANISM: Tetraselmis suecica

<400> SEQUENCE: 2

Met Gly Arg Gly Gly Phe Thr Asp Thr Pro Met Arg Gly Gly Ala Glu
1               5                   10                  15

Gly Glu Glu Val Leu Leu Lys Thr Lys Ala Gly Asp Val Gly Phe Leu
            20                  25                  30

Arg Thr Val Leu Arg Val Val Leu Asp Phe Asn Asn Ser Ala Ala Glu
        35                  40                  45

Asn Arg Ala Glu Tyr Tyr Lys Val Lys Lys Ala Ala Asp Glu Ala Lys
    50                  55                  60

Ala Ala Ala Gly Glu Arg Arg Thr Ser Arg Ala Lys Leu Glu Gln
65                  70                  75                  80

Lys Thr Ser Lys Val Ser Arg Ala Glu Val Ala Glu His Asn Asp Val
                85                  90                  95

His Asp Cys Trp Met Val Ile Lys Gly Lys Val Tyr Asp Val Thr Asp
            100                 105                 110

Phe Ala Ala Thr His Pro Gly Gly Arg Val Ile Tyr Thr Tyr Ala Gly
        115                 120                 125

Lys Asp Ala Thr Asp Val Phe Ala Ala Phe His Ala Gly Gly Thr Trp
    130                 135                 140

Ser Gln Leu Ser Glu Leu Gln Val Gly Glu Leu Ala Glu Glu Asp Ala
145                 150                 155                 160

Thr Lys Pro Glu Asp Pro Ile Val Gln Asp Phe Arg Asn Leu Arg Ala
                165                 170                 175

Lys Met Val Ala Glu Gly Leu Phe Lys Ser Asp Lys Leu Tyr Tyr Val
            180                 185                 190

Tyr Lys Thr Leu Ser Thr Leu Ser Ile Ala Leu Leu Ala Tyr Gly Ala
        195                 200                 205

Leu Ser Ala Trp Gly Ser Ser Leu Pro Gly Ile Leu Phe Ser Ala Phe
    210                 215                 220

Leu Leu Gly Leu Phe Trp Gln Gln Cys Gly Trp Leu Ala His Asp Phe
225                 230                 235                 240

Cys His Asn Gln Val Phe Arg Asn Arg Thr Tyr Asn Thr Trp Gly Gly
                245                 250                 255

Phe Leu Val Gly Ser Val Trp Gly Gly Phe Ser Val Asp Trp Trp Lys
            260                 265                 270

Gly Lys His Asn Thr His His Ala Ala Pro Asn Glu Ile Thr Ala Gly
        275                 280                 285

Gly Met Pro Val Asp Pro Asp Ile Asp Thr Leu Pro Leu Ile Ala Trp
    290                 295                 300

Ser Pro Glu Leu Leu Ser Asn Val His Asp Ala Ala Tyr Arg Ala Phe
305                 310                 315                 320

Ile Arg Leu Gln His Tyr Leu Phe Phe Pro Ile Leu Cys Phe Ala Arg
                325                 330                 335

Met Ser Trp Ala Gln Gln Ser Ala Thr His Pro Phe Asp Ala Ile Lys
            340                 345                 350

His Thr Ala Asn Val Gln Pro Arg Val Glu Lys Leu Ser Ile Ala Leu
        355                 360                 365

His Tyr Ala Trp Leu Leu Leu Phe Ala Phe Ser Gln Leu Pro Leu Leu
    370                 375                 380
```

```
Arg Gly Val Gly Phe Leu Leu Ala Ser Gln Met Met Ser Gly Ile Met
385                 390                 395                 400

Leu Ser Leu Val Phe Val Gln Ser His Asn Gly Met Glu Ile Tyr His
            405                 410                 415

Glu Pro Lys Asp Phe Phe Thr Ala Gln Leu Val Ser Thr Arg Asn Ile
        420                 425                 430

Phe Gly Ala Leu Ser Asp Arg Val Tyr Gly Pro Phe Asn Asp Trp Phe
    435                 440                 445

Thr Gly Gly Leu Asn Tyr Gln Ile Glu His His Leu Phe Pro Thr Met
450                 455                 460

Pro Arg His Arg Leu Ser Lys Ala Gln Val His Val Met Glu Val Cys
465                 470                 475                 480

Lys Lys His Gly Leu Val Tyr Glu Asn Cys Ser Met Thr Glu Gly Thr
                485                 490                 495

Val Arg Val Leu Ser Ala Leu Ala Asp Ile Ala Ala Leu Ala
            500                 505                 510

<210> SEQ ID NO 3
<211> LENGTH: 1533
<212> TYPE: DNA
<213> ORGANISM: Tetraselmis suecica

<400> SEQUENCE: 3
atgggcaggg gtgggtttac tgatacgccg atgcggggtg gggcggaggg ggaagaagtc      60
cttctgaaga ctaaggcggg cgacgtgggt tttctgagga ccgtcctccg cgtggtgctc     120
gacttcaaca actcggcggc cgagaaccgc gcggagtact ataaagtgaa gaaggcggcg     180
gatgaagcga aggcagctgc gggcgagcgt cgtcgcacca gccgcgccaa actggaacag     240
aagacgagta aagtgagccg tgcggaggta gcggaacaca cgatgtgca cgactgctgg      300 atggtcatca agggaaggt ctacgacgtg accgactttg cggcgacgca tcccggcggc      360
cgagtgatct acacctacgc ggggaaggac gccaccgacg tgtttgcggc cttccatgcc     420
ggaggcacct ggtcgcaact gtcggagctg caggtgggcg agctggccga ggaggatgcc     480
accaagcccg aggaccccat cgtgcaagat ttccgcaacc tgcagcaaa gatggttgca      540 gagggtttgt tcaagtcaga caagctgtac tacgtgtaca agaccctatc cactctgtcc     600
attgcgctgc tggcgtatgg ggcgctgtct cgtggggta gttccctgcc gggcatactc      660
ttctctgctt tcttgcttgg cctcttttgg cagcagtgcg gctggctcgc gcatgatttc     720
tgtcacaacc aggtgtttcg caatcggaca tacaacacat ggggtggctt ccttgtgggc     780
tctgtgtggg gcgggttcag tgtggactgg tggaagggga agcacaacac ccaccatgct     840
gcccccaatg agatcacggc cggtggcatg cctgtggacc cagacatcga cacgctgccc     900
ctgatcgcat ggagccctga gctgctatcc aacgtgcacg acgccgccta ccgcgccttc     960
atccgtctcc agcactacct cttcttcccc atcctctgct tgcccgtat gagctgggct    1020 cagcagagcg ccacgcaccc cttcgacgcc atcaagcaca ccgccaacgt tcagccccgc    1080
gttgagaagc tgtccattgc gctgcactat gcctggctac tcctctttgc cttcagccag    1140
ctccctctcc tccgcggcgt cggcttcctg ctcgccagcc agatgatgtc aggataatg     1200 ctcagcctgg tgttcgtgca gagccacaac gggatggaga tttaccacga gcccaaggat    1260
ttcttcacgg cgcagctcgt ctccacgcgc aacatattcg gtgcgttgag tgaccgagtc    1320 tacgcccct tcaacgattg gttcacgggt ggcctcaact atcagatcga gcatcacctc    1380 ttccccgacca tgcctcgcca ccgcctctcc aaggcgcagg tccacgtgat ggaggtgtgc    1440
```

```
aagaagcacg ggttggtgta tgagaactgc agcatgacag agggaacggt gcgggtgctc    1500
agcgcactgg cggacatcgc ggcacttgct tag                                 1533
```

<210> SEQ ID NO 4
<211> LENGTH: 510
<212> TYPE: PRT
<213> ORGANISM: Tetraselmis suecica

<400> SEQUENCE: 4

```
Met Gly Arg Gly Gly Phe Thr Asp Thr Pro Met Arg Gly Gly Ala Glu
 1               5                  10                  15

Gly Lys Glu Val Leu Leu Lys Thr Lys Ala Gly Asp Val Gly Phe Leu
            20                  25                  30

Arg Thr Val Leu Arg Val Val Leu Asp Phe Asn Asn Ser Ala Ala Glu
        35                  40                  45

Asn Arg Ala Glu Tyr Tyr Lys Val Lys Lys Ala Ala Asp Glu Ala Lys
    50                  55                  60

Ala Ala Ala Gly Glu Arg Arg Thr Ser Arg Ala Lys Leu Glu Gln
65                  70                  75                  80

Lys Thr Ser Lys Val Ser Arg Ala Glu Val Ala Glu His Asn Asp Val
                85                  90                  95

His Asp Cys Trp Met Ile Ile Lys Gly Lys Val Tyr Asp Val Thr Asp
            100                 105                 110

Phe Ala Ala Thr His Pro Gly Gly Arg Val Ile Tyr Thr Tyr Ala Gly
        115                 120                 125

Lys Asp Ala Thr Asp Val Phe Ala Ala Phe His Ala Gly Gly Thr Trp
    130                 135                 140

Ser Gln Leu Ser Glu Leu Gln Val Gly Glu Leu Thr Glu Glu Asp Ala
145                 150                 155                 160

Thr Lys Pro Glu Asp Pro Ile Val Gln Asp Phe Arg Asn Leu Arg Ala
                165                 170                 175

Lys Met Val Ala Glu Gly Leu Phe Lys Ser Asp Lys Leu Tyr Tyr Val
            180                 185                 190

Tyr Lys Thr Leu Ser Thr Leu Ser Ile Ala Leu Leu Ala Tyr Gly Ala
        195                 200                 205

Leu Phe Ala Trp Gly Ser Ser Leu Pro Gly Met Leu Phe Ser Ala Phe
    210                 215                 220

Leu Leu Gly Leu Phe Trp Gln Gln Cys Gly Trp Leu Ala His Asp Phe
225                 230                 235                 240

Cys His Asn Gln Val Phe Arg Asn Arg Thr Tyr Asn Thr Trp Gly Gly
                245                 250                 255

Phe Leu Val Gly Ser Val Trp Gly Gly Phe Ser Val Asp Trp Trp Lys
            260                 265                 270

Gly Lys His Asn Thr His His Ala Ala Pro Asn Glu Ile Thr Ala Gly
        275                 280                 285

Gly Met Pro Val Asp Pro Asp Ile Asp Thr Leu Pro Leu Ile Ala Trp
    290                 295                 300

Ser Pro Glu Leu Leu Ser Asn Val His Asp Ala Ala Tyr Arg Ala Phe
305                 310                 315                 320

Ile Arg Leu Gln His Tyr Leu Phe Phe Pro Ile Leu Cys Phe Ala Arg
                325                 330                 335

Met Ser Trp Ala Gln Gln Ser Ala Thr His Pro Phe Asp Ala Ile Lys
            340                 345                 350

His Thr Ala Asn Val Gln Pro Arg Val Glu Lys Leu Ser Ile Ala Leu
        355                 360                 365
```

His Tyr Ala Trp Leu Leu Phe Ala Phe Ser Gln Leu Pro Leu Leu
    370                 375                 380

Arg Gly Val Gly Phe Leu Leu Ala Ser Gln Met Met Ser Gly Ile Met
385                 390                 395                 400

Leu Ser Leu Val Phe Val Gln Ser His Asn Gly Met Glu Ile Tyr His
                405                 410                 415

Glu Pro Lys Asp Phe Phe Thr Ala Gln Leu Val Ser Thr Arg Asn Ile
            420                 425                 430

Phe Gly Ala Leu Ser Asp Arg Val Tyr Gly Pro Phe Asn Asp Trp Phe
        435                 440                 445

Thr Gly Gly Leu Asn Tyr Gln Ile Glu His His Leu Phe Pro Thr Met
    450                 455                 460

Pro Arg His Arg Leu Ser Lys Ala Gln Val His Val Met Glu Val Cys
465                 470                 475                 480

Lys Lys His Gly Leu Val Tyr Glu Asn Cys Ser Met Thr Glu Gly Thr
                485                 490                 495

Val Arg Val Leu Ser Ala Leu Ala Asp Ile Ala Ala Leu Ala
            500                 505                 510

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
tggtggaarr msaagcayaa c                                           21

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
ardccwccvb draaccarty                                             20

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
agtagccagg catagtgcag cgcaat                                      26

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
ttcaacgatt ggttcacggg tggc                                        24

<210> SEQ ID NO 9
<211> LENGTH: 25
<212> TYPE: DNA

-continued

```
<213> ORGANISM: Artificial
<220> FEATURE:
<223> OTHER INFORMATION: Primer

<400> SEQUENCE: 9
aacatgggca ggggtgggtt tactg                                          25

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
ctaagcaagt gccgcgatgt ccg                                            23

<210> SEQ ID NO 11
<211> LENGTH: 442
<212> TYPE: PRT
<213> ORGANISM: Isochrysis galbana

<400> SEQUENCE: 11
```

Met Val Ala Gly Lys Ser Gly Ala Ala His Val Thr His Ser Ser
1               5                   10                  15

Thr Leu Pro Arg Glu Tyr His Gly Ala Thr Asn Asp Ser Arg Ser Glu
            20                  25                  30

Ala Ala Asp Val Thr Val Ser Ser Ile Asp Ala Glu Lys Glu Met Ile
        35                  40                  45

Ile Asn Gly Arg Val Tyr Asp Val Ser Ser Phe Val Lys Arg His Pro
    50                  55                  60

Gly Gly Ser Val Ile Lys Phe Gln Leu Gly Ala Asp Ala Ser Asp Ala
65                  70                  75                  80

Tyr Asn Asn Phe His Val Arg Ser Lys Lys Ala Asp Lys Met Leu Tyr
                85                  90                  95

Ser Leu Pro Ser Arg Pro Ala Glu Ala Gly Tyr Ala Gln Asp Asp Ile
            100                 105                 110

Ser Arg Asp Phe Glu Lys Leu Arg Leu Glu Leu Lys Glu Glu Gly Tyr
        115                 120                 125

Phe Glu Pro Asn Leu Val His Val Ser Tyr Arg Cys Val Glu Val Leu
    130                 135                 140

Ala Met Tyr Trp Ala Gly Val Gln Leu Ile Trp Ser Gly Tyr Trp Phe
145                 150                 155                 160

Leu Gly Ala Ile Val Ala Gly Ile Ala Gln Gly Arg Cys Gly Trp Leu
                165                 170                 175

Gln His Glu Gly Gly His Tyr Ser Leu Thr Gly Asn Ile Lys Ile Asp
            180                 185                 190

Arg His Leu Gln Met Ala Ile Tyr Gly Leu Gly Cys Gly Met Ser Gly
        195                 200                 205

Cys Tyr Trp Arg Asn Gln His Asn Lys His His Ala Thr Pro Gln Lys
    210                 215                 220

Leu Gly Thr Asp Pro Asp Leu Gln Thr Met Pro Leu Val Ala Phe His
225                 230                 235                 240

Lys Ile Val Gly Ala Lys Ala Arg Gly Lys Gly Lys Ala Trp Leu Ala
                245                 250                 255

Trp Gln Ala Pro Leu Phe Phe Gly Gly Ile Ile Cys Ser Leu Val Ser
            260                 265                 270

Phe Gly Trp Gln Phe Val Leu His Pro Asn His Ala Leu Arg Val His

```
                275                 280                 285
Asn His Leu Glu Leu Ala Tyr Met Gly Leu Arg Tyr Val Leu Trp His
            290                 295                 300
Leu Ala Phe Gly His Leu Gly Leu Leu Ser Ser Leu Arg Leu Tyr Ala
305                 310                 315                 320
Phe Tyr Val Ala Val Gly Gly Thr Tyr Ile Phe Thr Asn Phe Ala Val
                325                 330                 335
Ser His Thr His Lys Asp Val Val Pro Pro Thr Lys His Ile Ser Trp
            340                 345                 350
Ala Leu Tyr Ser Ala Asn His Thr Thr Asn Cys Ser Asp Ser Pro Phe
                355                 360                 365
Val Asn Trp Trp Met Ala Tyr Leu Asn Phe Gln Ile Glu His His Leu
            370                 375                 380
Phe Pro Ser Met Pro Gln Tyr Asn His Pro Lys Ile Ala Pro Arg Val
385                 390                 395                 400
Arg Ala Leu Phe Glu Lys His Gly Val Glu Tyr Asp Val Arg Pro Tyr
                405                 410                 415
Leu Glu Cys Phe Arg Val Thr Tyr Val Asn Leu Leu Ala Val Gly Asn
            420                 425                 430
Pro Glu His Ser Tyr His Glu His Thr His
            435                 440

<210> SEQ ID NO 12
<211> LENGTH: 457
<212> TYPE: PRT
<213> ORGANISM: Mortierella alpina

<400> SEQUENCE: 12

Met Ala Ala Ala Pro Ser Val Arg Thr Phe Thr Arg Ala Glu Val Leu
1               5                   10                  15
Asn Ala Glu Ala Leu Asn Glu Gly Lys Lys Asp Ala Glu Ala Pro Phe
            20                  25                  30
Leu Met Ile Ile Asp Asn Lys Val Tyr Asp Val Arg Glu Phe Val Pro
        35                  40                  45
Asp His Pro Gly Gly Ser Val Ile Leu Thr His Val Gly Lys Asp Gly
    50                  55                  60
Thr Asp Val Phe Asp Thr Phe His Pro Glu Ala Ala Trp Glu Thr Leu
65                  70                  75                  80
Ala Asn Phe Tyr Val Gly Asp Ile Asp Glu Ser Asp Arg Asp Ile Lys
                85                  90                  95
Asn Asp Asp Phe Ala Ala Glu Val Arg Lys Leu Arg Thr Leu Phe Gln
            100                 105                 110
Ser Leu Gly Tyr Tyr Asp Ser Ser Lys Ala Tyr Tyr Ala Phe Lys Val
        115                 120                 125
Ser Phe Asn Leu Cys Ile Trp Gly Leu Ser Thr Val Ile Val Ala Lys
    130                 135                 140
Trp Gly Gln Thr Ser Thr Leu Ala Asn Val Leu Ser Ala Ala Leu Leu
145                 150                 155                 160
Gly Leu Phe Trp Gln Gln Cys Gly Trp Leu Ala His Asp Phe Leu His
                165                 170                 175
His Gln Val Phe Gln Asp Arg Phe Trp Gly Asp Leu Phe Gly Ala Phe
            180                 185                 190
Leu Gly Gly Val Cys Gln Gly Phe Ser Ser Ser Trp Trp Lys Asp Lys
        195                 200                 205
His Asn Thr His His Ala Ala Pro Asn Val His Gly Glu Asp Pro Asp
```

```
            210                 215                 220
Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
                260                 265                 270

Arg Leu Ser Trp Cys Leu Gln Ser Ile Leu Phe Val Leu Pro Asn Gly
            275                 280                 285

Gln Ala His Lys Pro Ser Gly Ala Arg Val Pro Ile Ser Leu Val Glu
            290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
                340                 345                 350

Asn Gly Met Pro Val Ile Ser Lys Glu Glu Ala Val Asp Met Asp Phe
            355                 360                 365

Phe Thr Lys Gln Ile Ile Thr Gly Arg Asp Val His Pro Gly Leu Phe
            370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
            435                 440                 445

Ala Ala Ser Lys Met Gly Lys Ala Gln
            450                 455

<210> SEQ ID NO 13
<211> LENGTH: 1290
<212> TYPE: DNA
<213> ORGANISM: Neurospora crassa

<400> SEQUENCE: 13
atggctgtca ctactaggtc acacaaagcc gccgctgcca ccgaacctga agttgtgtct      60
acaggagtgg atgcagtcag cgctgccgca ccaagcagta gtagctcctc atcctcccaa     120
aagtcagctg agcctatcga atatccagac atcaagacaa ttcgtgacgc tataccagac     180
cactgcttta gacctcgcgt tggatatact atggcgtact ttattcgcga ttttgcaatg     240
gctttcggcc tcggatactt ggcatggcaa tacatccctt tgattgcaag taccccattg     300
agatacggag cttgggcttt gtacggttac ctccagggac tcgtctgtac tggaatttgg     360
atcttggctc acgaatgcgg tcacggagcc ttttctagac acacctggtt caacaacgtt     420
atgggttgga ttggtcactc tttcctacta gtcccatatt ttagctggaa attttcccat     480
caccgtcatc ataggttcac cggacatatg gaaaagata tggcgttcgt tccagccacg      540
gaggcggaca gaaatcagag aaaactagct aatctctata tggacaaaga gactgcggag     600
atgttcgagg atgttcctat tgtgcagttg gttaaactaa ttgctcacca actcgccggt     660
tggcagatgt atctcttgtt caacgttagt gccggaaaag ctccaaaaca gtgggaaacc     720
ggcaaaggtg gaatgggatg gctccgcgtg agccatttcg aaccaagttc agccgttttc     780
```

```
agaaacagcg aagcaattta catagctcta agcgatctcg gacttatgat tatgggatac    840
attctctacc aggcagccca agttgttgga tggcaaatgg ttggtctctt gtattttcaa    900
cagtacttct gggttcacca ttggctcgtt gccatcactt accttcatca cacacacgaa    960
gaagttcacc actttgatgc agattcttgg acatttgtta agggtgccct cgctaccgtg   1020
gacagagact tcggtttcat cggcaagcac ctcttccata acatcattga ccatcatgtt   1080
gttcatcacc tcttcccaag aatcccttc tactacgctg aagaagctac caattcaata   1140
agacctatgc tcggacctct ttaccacaga gatgaccgtt ctttcatggg gcaactctgg   1200
tacaacttca cacactgcaa atgggttgtc cctgatcctc aagtgccagg tgctctaatc   1260
tgggctcaca ccgttcagag tactcagtaa                                    1290

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
gtcgacaaac aatgggcagg ggtgggttta                                      30

<210> SEQ ID NO 15
<211> LENGTH: 29
<212> TYPE: DNA
<213> ORGANISM: Artificial
<220> FEATURE:
<223> OTHER INFORMATION: Primer

<400> SEQUENCE: 15
cctgcaggct aagcaagtgc cgcgatgtc                                       29

<210> SEQ ID NO 16
<211> LENGTH: 25
<212> TYPE: DNA
<213> ORGANISM: Artificial
<220> FEATURE:
<223> OTHER INFORMATION: Primer

<400> SEQUENCE: 16
aaaaatgggc aggggtgggt ttact                                           25

<210> SEQ ID NO 17
<211> LENGTH: 1289
<212> TYPE: DNA
<213> ORGANISM: Neurospora crassa

<400> SEQUENCE: 17
tggcggtcac cacccgcagc cacaaggccg cggccgccac cgagcccgag gttgtcagca     60
ccggcgttga cgccgtctct gctgctgctc cctcctcctc ctcctcctct tccagccaaa    120
agtcggccga gcccatcgaa taccccgaca tcaagaccat ccgcgacgcc atccccgacc    180
actgcttccg cccgcgcgtc tggatctcca tggcctactt catccgcgac ttcgccatgg    240
cctttggcct cggctacctc gcctggcagt acatcccct gatcgcctcc accccgctcc    300 gctacgcgc ctgggctctg tacggctacc tccagggtct cgtctgcacg ggcatctgga    360
ttctggcgca cgagtgcggc cacggcgcct tctcgaggca cacgtggttc aacaacgtca    420
tggggtggat tggccactcc ttcctcttgg tcccttactt cagctggaag ttcagccacc    480
atcgccacca tcgcttcacc ggccacatgg agaaggacat ggcgtttgtg cctgccaccg    540
```

```
aggctgatcg caaccagagg aagctggcca acttgtacat ggacaaggag acggccgaga    600
tgtttgagga tgtgcccatt gtccagctcg tcaagctcat cgcccaccag ctggccggct    660
ggcagatgta cctcctcttc aacgtctccg ccggtaaggg cagcaagcag tgggagactg    720
gcaagggcgg catgggctgg ttgagggtta gccactttga gccttcctct gctgtgttcc    780
gcaactccga ggccatctac attgcccgt ccgatcttgg tctcatgatc atgggctaca    840
tcctctacca ggccgcgcag gttgttggct ggcagatggt gggtctgctg tacttccagc    900
agtacttctg ggttcaccat tggttggtcg ccatcactta cctccaccac acccacgagg    960
aagtccacca ctttgacgcc gactcgtgga ccttcgtcaa gggcgctctc gccaccgtcg   1020
accgcgattt tggcttcatt ggcaagcacc tcttccacaa cattatcgac caccacgtcg   1080
tccaccactt gttccctcgc atccccttct actacgccga agaagccacc aactcgatcc   1140
gccccatgct cggcccccctc taccaccgcg acgaccgctc cttcatgggc agctgtggt   1200 acaacttcac ccactgcaag tgggtcgttc cggaccccca ggtccccggc gcgcttattt   1260
gggcgcacac cgttcagagc acccagtaa                                    1289

<210> SEQ ID NO 18
<211> LENGTH: 1533
<212> TYPE: DNA
<213> ORGANISM: Tetraselmis suecica

<400> SEQUENCE: 18
atgggccgcg gtggctttac tgatacgccg atgcgcggtg cgctgaggg cgaagaagtc      60 cttctcaaga ctaaggcggg tgacgtcggt ttcctgagga ccgtcctccg cgtcgtgctc    120
gacttcaaca actcggcggc cgagaaccgc gcggagtatt ataaagtcaa gaaggcggcg    180
gatgaagcga aggccgctgc gggcgagcgt cgtcgcacca gccgcgccaa actggaacag    240
aagacgagta agtgagccg tgcggaggtg gcggaacaca acgatgtgca cgactgctgg    300
atggtcatca aaggcaaggt ctacgacgtg accgactttg cggctacgca tcccggtggc    360
cgagtgatct acacctacgc gggcaaggac gccaccgacg tgtttgcggc cttccatgcc    420
ggaggcacct ggtcgcaact gtcggagctg caagtgggcg agctggccga ggaggatgcc    480
accaagcccg aggaccctat cgtgcaagat ttccgcaacc tgcgagcaaa gatggttgca    540
gagggtttgt tcaagtcaga caagctgtac tacgtgtaca agaccctatc cactctgtcc    600
attgcgctgc tggcgtatgg cgcgctgtct gcgtggggta gttccctgcc gggcatactc    660
ttctctgctt tcttgcttgg cctcttctgg cagcagtgcg gctggctcgc gcatgatttc    720
tgtcacaacc aagtgtttcg caatcggacc tacaacacct ggggtggctt ccttgtgggc    780
tctgtgtggg gtggcttcag tgtggactgg tggaagggca agcacaacac gcaccatgct    840
gcgcccaatg agatcaccggc cggtgggatg cctgtggacc cagacatcga cacgctgccg    900
ctgatcgcat ggagccctga gctgctatcc aacgtgcacg acgccgccta ccgcgccttc    960
atccgtctcc agcactacct cttcttcccg atcctctgct tgcccgtat gagctgggct   1020 cagcagagcg ccacgcaccc gttcgacgcc atcaagcaca ccgccaacgt tcagccgcgc   1080
gttgagaagc tgtccattgc gctgcactat gcctggctac tcctcttgc cttcagccag   1140 ctccctctcc tgcgcggcgt cggcttcctg ctcgccagcc agatgatgtc aggataatg   1200 ctcagcctgg tcttcgtgca gagccacaac gggatggaga tctaccacga gcccaaggat   1260
ttcttcacgg cgcagctcgt ctccacgcgc aacatattcg gtgcgttgag tgaccgagtg   1320
tacggcccgt tcaacgattg gttcacgggt ggcctcaact atcagatcga gcatcacctc   1380
```

```
ttcccgacca tgcctcgcca ccgcctctcc aaggcgcaag tgcacgtgat ggaggtctgc    1440
aagaagcacg gcttggtgta cgagaactgc tccatgacag agggaacggt gcgggtgctc    1500
agcgcactgg cggacatcgc ggcacttgct tga                                 1533

<210> SEQ ID NO 19
<211> LENGTH: 1212
<212> TYPE: DNA
<213> ORGANISM: Mortierella alpina

<400> SEQUENCE: 19
atggcgccac cacacgtagt agacgaacag gtgaggcgta gaattgttgt cgaggacgag      60
ataaagtcca agaagcagtt tgagaggaac tacgttccaa tggacttcac cattaaggaa     120
ataagggatg ccattcccgc acatctattc attcgagaca ccaccaaaag tatcctccac     180
gtagttaagg atctcgtgac catagcgatc gtgttttact gcgccacatt cattgagact     240
ttgccatcct tagctctacg tgtaccagct tggattacat actggatcat ccaaggaact     300
gtgatggttg ggccatggat acttgcccac gagtgcggac atggggcctt ctctgactcc     360
aagaccatta acacaatttt cggctgggtt ctgcactccg ccctattggt accataccag     420
gcctgggcta tgtctcactc taaacaccac aaaggtacag ggtccatgac caaggacgtt     480
gttttcatcc cagccactag gtcctacaag ggtcttcctg ctctcgagaa acctgctgtg     540
gaggaagagg tttctgaaca ggaacaccac caccacgagg agtctatctt cgcggagact     600
ccaatctaca ctcttggtgc gttgctcttt gtgctcacct tcgggtggcc cctctaccta     660
attgtgaact tttctggaca cgaagcacca cactgggtga accacttcca aacagtcgca     720
ccattgtacg agccccatca aaggaagaac atctttttact cgaattgcgg aatcgtggcc     780
atgggatcga tacttaccta cctctcgatg gtgttcagtc ctttgactgt tttcatgtac     840
tatggcattc cttacctcgg agttaacgca tggattgtgt gcatcactta tctgcaacac     900
accgatccaa aagtcccaca cttccgagat aacgaatgga actttcaacg cggggccgct     960
tgcaccatag atcgttcctt tggaaccatt gtcaaccatc tacatcacca catagtgac    1020 tctcaccaat gtcatcacat gttctcccag atgccctttt acaacgcggt cgaagccact    1080
aaatacttaa aggccaagct tgggaagtac tacatcttcg acgataccc aatagcaaag    1140 gctctttacc ggaactggcg cgaatgcaaa ttcgttgaag atgagggaga tgtggtgttc    1200
tacaagcact aa                                                        1212

<210> SEQ ID NO 20
<211> LENGTH: 34
<212> TYPE: DNA
<213> ORGANISM: Artificial
<220> FEATURE:
<223> OTHER INFORMATION: Primer

<400> SEQUENCE: 20
gtcgacaaac aatggcgcca ccacacgtag taga                                 34

<210> SEQ ID NO 21
<211> LENGTH: 35
<212> TYPE: DNA
<213> ORGANISM: Artificial
<220> FEATURE:
<223> OTHER INFORMATION: Primer

<400> SEQUENCE: 21
cctgcaggtt agtgcttgta gaacaccaca tctcc                                35
```

```
<210> SEQ ID NO 22
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 22

Gln Xaa Xaa His His
1               5

<210> SEQ ID NO 23
<211> LENGTH: 23
<212> TYPE: DNA
<213> ORGANISM: Artificial
<220> FEATURE:
<223> OTHER INFORMATION: Synthetic primer

<400> SEQUENCE: 23
cgactggagc acgaggacac tga                                           23

<210> SEQ ID NO 24
<211> LENGTH: 25
<212> TYPE: DNA
<213> ORGANISM: Artificial
<220> FEATURE:
<223> OTHER INFORMATION: Synthetic primer

<400> SEQUENCE: 24
gctgtcaacg atacgctacg taacg                                         25
```

FATTY ACID DESATURASES FROM *TETRASELMIS SUECICA*

This application claims the priority of U.S. Provisional Patent Application Ser. No. 60/831,838, filed Jul. 19, 2006, the entire disclosure of which is specifically incorporated herein by reference.

BACKGROUND OF THE INVENTION

1. Field of the Invention

The invention relates generally to desaturase enzymes that modulate the number and location of double bonds in long chain poly-unsaturated fatty acids (LC-PUFA's). In particular, the invention relates to improvement of fatty acid profiles using delta 6 desaturase enzymes and nucleic acids encoding such desaturase enzymes.

2. Description of the Related Art

The primary products of fatty acid biosynthesis in most organisms are 16- and 18-carbon compounds. The relative proportion of chain lengths and degree of unsaturation of these fatty acids vary widely among species. Mammals, for example, produce primarily saturated and monounsaturated fatty acids, while most higher plants produce fatty acids with one, two, or three double bonds, the latter two comprising polyunsaturated fatty acids (PUFA's).

Two main families of PUFAs are the omega-3 fatty acids (also represented as "n-3" fatty acids), exemplified by stearidonic acid (SDA, 18:4, n-3), and the omega-6 fatty acids (also represented as "n-6" fatty acids), exemplified by 7-linolenic acid (GLA, 18:3, n-6). PUFAs are important components of the plasma membrane of the cell and adipose tissue, where they may be found in such forms as phospholipids and as triglycerides, respectively. PUFAs are necessary for proper development in mammals, particularly in the developing infant brain, and for tissue formation and repair.

Several disorders respond to treatment with fatty acids. Supplementation with PUFAs has been shown to reduce the rate of restenosis after angioplasty. The health benefits of certain dietary omega-3 fatty acids for cardiovascular disease and rheumatoid arthritis also have been well documented (Simopoulos et al., 1999; James et al., 2000). Further, PUFAs have been suggested for use in treatments for asthma and psoriasis. Evidence indicates that PUFAs may be involved in calcium metabolism, suggesting that PUFAs may be useful in the treatment or prevention of osteoporosis and of kidney or urinary tract stones. The majority of evidence for health benefits applies to the long chain omega-3 fats, eicosapentaenoic acid (EPA, 20:5, n-3) and docosahexaenoic acid (DHA, 22:6, n-3) which are found in fish and fish oil. With this base of evidence, health authorities and nutritionists in Canada (Scientific Review Committee, 1990, Nutrition Recommendations, Minister of National Health and Welfare, Ottawa, Canada), Europe (de Deckerer, *Eur. J. Clin. Nutr.*, 52:749, 1998), the United Kingdom (The British Nutrition Foundation, 1992, Unsaturated fatty-acids—nutritional and physiological significance: The report of the British Nutrition Foundation's Task Force, Chapman and Hall, London), and the United States (Simopoulos et al., 1999) have recommended increased dietary consumption of these PUFAs.

PUFAs also can be used to treat diabetes (U.S. Pat. No. 4,826,877; Horobin et al., 1993). Altered fatty acid metabolism and composition have been demonstrated in diabetic animals. These alterations have been suggested to be involved in some of the long-term complications resulting from diabetes, including retinopathy, neuropathy, nephropathy and reproductive system damage. Primrose oil, which contains GLA, has been shown to prevent and reverse diabetic nerve damage. Administration of an omega-3 fatty acid, such as SDA, has been shown to inhibit biosynthesis of leukotrienes (U.S. Pat. No. 5,158,975). The consumption of SDA has been shown to lead to a decrease in blood levels of proinflammatory cytokines TNF-α and IL-1β (PCT US 0306870).

PUFAs, such as linoleic acid (LA, 18:2, Δ9, 12) and α-linolenic acid (ALA, 18:3, Δ9, 12, 15), are regarded as essential fatty acids in the diet because mammals lack the ability to synthesize these acids. LA is produced from oleic acid (OA, 18:1, Δ9) by a Δ12-desaturase while ALA is produced from LA by a Δ15-desaturase. However, when ingested, mammals have the ability to metabolize LA and ALA to form the n-6 and n-3 families of long-chain polyunsaturated fatty acids (LC-PUFA). These LC-PUFA's are important cellular components conferring fluidity to membranes and functioning as precursors of biologically active eicosanoids such as prostaglandins, prostacyclins, and leukotrienes, which regulate normal physiological functions. Arachidonic acid (ARA, 20:4, n-6) is the principal precursor for the synthesis of eicosanoids, which include leukotrienes, prostaglandins, and thromboxanes, and which also play a role in the inflammation process.

In mammals, the formation of LC-PUFA is rate-limited by the step of Δ6 desaturation, which converts LA to GLA and ALA to SDA. Many physiological and pathological conditions have been shown to depress this metabolic step even further, and consequently, the production of LC-PUFA. To overcome the rate-limiting step and increase tissue levels of EPA, one could consume large amounts of ALA. However, consumption of just moderate amounts of SDA provides an efficient source of EPA, as SDA is about four times more efficient than ALA at elevating tissue EPA levels in humans (U.S. Patent Publication 20040039058 (Ursin et al.). In the same studies, SDA administration was also able to increase the tissue levels of docosapentaenoic acid (DPA), which is an elongation product of EPA. Alternatively, bypassing the Δ6-desaturation via dietary supplementation with EPA or DHA can effectively alleviate many pathological diseases associated with low levels of PUFA. However, as set forth in more detail below, currently available sources of PUFA are not desirable for a multitude of reasons. The need for a reliable and economical source of PUFA's has spurred interest in alternative sources of PUFA's.

Major long chain PUFAs of importance include DHA and EPA, which are primarily found in different types of fish oil, and ARA, found in filamentous fungi such as *Mortierella*. For DHA, a number of sources exist for commercial production including a variety of marine organisms, oils obtained from cold water marine fish, and egg yolk fractions. Commercial sources of SDA include the plant genera *Trichodesma*, *Borago* (borage) and *Echium*. Commercial sources of GLA include the plant genera *Borago, Oenothera* and *Ribes*. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFAs.

Natural sources of PUFAs also are subject to uncontrollable fluctuations in availability. Fish stocks may undergo natural variation or may be depleted by over fishing. In addition, even with overwhelming evidence of their therapeutic benefits, dietary recommendations regarding omega-3 fatty acids are not heeded. Fish oils have unpleasant tastes and odors, which may be impossible to economically separate from the desired product, and can render such products unacceptable as food supplements. Animal oils, and particularly fish oils, can accumulate environmental pollutants. Foods may be enriched with fish oils, but again, such enrichment is problematic because of cost and declining fish stocks worldwide. This problem is also an impediment to consumption and intake of whole fish. Nonetheless, if the health messages to increase fish intake were embraced by communities, there would likely be a problem in meeting demand for fish. Furthermore, there are problems with sustainability of this industry, which relies heavily on wild fish stocks for aquaculture feed (Naylor et al., 2000).

Other natural limitations favor a novel approach for the production of PUFAs. Weather and disease can cause fluctuation in yields from both fish and plant sources. Cropland available for production of alternate oil-producing crops is subject to competition from the steady expansion of human populations and the associated increased need for food production on the remaining arable land. Crops that do produce PUFAs, such as borage, have not been adapted to commercial growth and may not perform well in monoculture. Growth of such crops is thus not economically competitive where more profitable and better-established crops can be grown. Large-scale fermentation of organisms such as *Mortierella* is also expensive. Natural animal tissues contain low amounts of ARA and are difficult to process. Microorganisms such as *Porphyridium* and *Mortierella* are difficult to cultivate on a commercial scale.

Therefore, it would be advantageous to obtain genetic material involved in PUFA biosynthesis and to express the isolated material in a plant system, in particular, a land-based terrestrial crop plant system, which can be manipulated to provide production of commercial quantities of one or more PUFA's. In commercial oilseed crops, such as canola, soybean, corn, sunflower, safflower, or flax, the conversion of some fraction of the mono and polyunsaturated fatty acids that typify their seed oil to SDA and GLA requires the seed-specific expression of multiple desaturase enzymes that includes delta 6- and delta 15-desaturases. Oils derived from plants expressing elevated levels of Δ6- and Δ15-desaturases are rich in SDA and GLA. As there is also a need to increase omega-3 fatty acid intake in humans and animals, there is a need to provide a wide range of omega-3 enriched foods and food supplements so that subjects can choose feed, feed ingredients, food and food ingredients which suit their usual dietary habits. It is also advantageous to provide commercial quantities of GLA. Thus, there exists a strong need for novel nucleic acids of Δ6-desaturases for use in transgenic crop plants with oils enriched in PUFAs, as well as the improved food and feeds produced thereby.

SUMMARY OF THE INVENTION

In one aspect, the invention provides isolated nucleic acids encoding a polypeptide capable of desaturating a fatty acid molecule at carbon 6. These may be used to transform cells or modify the fatty acid composition of a plant or the oil produced by a plant. One embodiment of the invention is isolated polynucleotide sequences isolated from *Tetraselmis suecica* having unique desaturase activity. In certain further embodiments of the invention, the polynucleotides encode a polypeptide having at least 75% sequence identity to the polypeptide sequence of SEQ ID NO:2 or SEQ ID NO:4, including at least about 80%, 82%, 85%, 87%, 90%, 92%, 95%, 98% and 99% homology to these sequences. Those of skill in the art will recognize that, as these sequences are related, a given polypeptide may simultaneously share 75% or greater homology to more than one of these polypeptide sequences.

In another aspect, the invention provides an isolated polynucleotide that encodes a polypeptide having desaturase activity that desaturates a fatty acid molecule at carbon 6, comprising a sequence selected from the group consisting of: (a) a polynucleotide encoding the polypeptide of SEQ ID NO:2 or SEQ ID NO:4; (b) a polynucleotide comprising the nucleic acid sequence of SEQ ID NO:1 or SEQ ID NO:3; (c) a polynucleotide hybridizing to SEQ ID NO:1 or SEQ ID NO:3, or a complement thereof, under conditions of 5×SSC, 50% formamide and 42° C.; and (d) a polynucleotide encoding a polypeptide with at least 75%, 85%, 95%, 98%, or 99% sequence identity to a polypeptide sequence of SEQ ID NO:2 or SEQ ID NO:4. In another aspect, the invention provides an isolated polypeptide comprising the polypeptide sequences of SEQ ID NO:2 or SEQ ID NO:4 or a fragment thereof having desaturase activity that desaturates a fatty acid molecule at carbon 6.

In yet another aspect, the invention provides a DNA construct comprising the isolated polynucleotide that encodes a polypeptide having desaturase activity that desaturates a fatty acid molecule at carbon 6, comprising a sequence selected from the group consisting of: (a) a polynucleotide encoding the polypeptide of SEQ ID NO:2 or SEQ ID NO:4; (b) a polynucleotide comprising the nucleic acid sequence of SEQ ID NO:1 or SEQ ID NO:3; (c) a polynucleotide hybridizing to SEQ ID NO:1 or SEQ ID NO:3, or a complement thereof, under conditions of 5×SSC, 50% formamide and 42° C.; and (d) a polynucleotide encoding a polypeptide with at least 75%, 85%, 95%, 98%, or 99% sequence identity to a polypeptide sequence of SEQ ID NO:2 or SEQ ID NO:4. In a further embodiment, the DNA construct further comprises a heterologous promoter operably linked to the isolated polynucleotide described above. In other embodiments, the promoter is functional in a prokaryotic cell or a eukaryotic cell. In certain embodiments, the eukaryotic cell in which the promoter is functional is a plant cell. In a further embodiment, the promoter is a seed-enhanced promoter. In yet another embodiment, the DNA construct further comprises at least one additional polynucleotide sequence encoding a fatty acid desaturase.

In still yet another aspect, the invention provides a host cell transformed with a DNA construct comprising the isolated polynucleotide that encodes a polypeptide having desaturase activity that desaturates a fatty acid molecule at carbon 6 provided by the invention. The host cell may be a plant, animal, fungal or bacterial cell. In a further embodiment, the host cell of the invention provides a host cell that exhibits altered fatty acid biosynthesis relative to a cell of the same genotype as the host cell but lacking the DNA construct. In yet another aspect, the host cell has inherited the DNA construct from a progenitor of the cell.

In still yet another aspect, the invention provides a plant and its progeny comprising the host cells transformed with a DNA construct of the invention. Such a plant may be defined as comprising altered fatty acid metabolism relative to a plant of the same genotype lacking the DNA construct. In yet another aspect, such a plant may further comprise at least one additional polynucleotide sequence encoding a fatty acid desaturase. In one embodiment, the plant is selected from the group consisting of canola, *Brassica campestris*, oilseed rape, rapeseed, soybean, crambe, mustard, castor bean, peanut, sesame, cottonseed, linseed, safflower, oil palm, flax, sunflower, corn, rice, barley, millet, rye, wheat, oat, alfalfa and sorghum. The invention also provides seed of the plant of the invention. In another aspect, the invention provides an oil composition extracted from corn seed comprising a GLA content from about 5% to about 15%, about 20%, or about 26% by weight of total fatty acids. In one embodiment, the oil composition further comprises an SDA content of from about 3% to about 13% by weight of total fatty acids, including intermediate SDA content, such as about 5%, about 8%, or about 10% SDA content by weight of total fatty acids. The invention is also embodied by an oil composition extracted from corn seed comprising a GLA content of at least about 3%, at least about 5%, or at least about 10% by weight of total fatty acids; and an SDA content of at least about 3%, about 5%, about 8%, about 10%, about 13%, or about 20% by weight of total fatty acids, wherein the ratio of GLA/SDA is between about 1.3 and about 3.7. In yet another aspect, the invention provides an oil composition extracted from soybean seed having a GLA content from about 9% to about 51% by weight of total fatty acids, including about 20%, about 30%, or about 40% by weight of total fatty acids. In one embodiment, the oil composition further comprises an SDA content of from about 0.5% to about 10% by weight of total fatty acids. The invention is also embodied by an oil composition extracted from soybean seed comprising a GLA content of at least about 1%, about 3%, about 5%, about 10%, about 13%, or about 20% by weight of total fatty acids and an SDA content of at least about 1% by weight of total fatty acids, wherein the ratio of GLA/SDA is between about 2.8 and about 18.3.

In still yet another aspect, the invention provides a method of producing food or feed, comprising the steps of (a) obtaining the transgenic plant of the invention; and (b) producing the food or feed. The food or feed may be oil, silage, meal, grain, starch, flour or protein. The food or feed composition is defined as comprising a detectable polynucleotide sequence or detectable polypeptide provided by the invention. Additionally, the invention provides animal feed and human food compositions comprising GLA or SDA.

In still yet another aspect, the invention provides a method of increasing the nutritional value of an edible product for human or animal consumption, comprising adding transformed plants or plant parts, or derivatives thereof provided by the invention to the edible product. In certain embodiments, the product is human and/or animal food. The edible product may also be animal feed and/or a food supplement.

In still yet another aspect, the invention provides a method of manufacturing food or feed, comprising adding transformed plants or plant parts, or derivatives thereof provided by the invention to starting food or feed ingredients to produce the food or feed. In certain embodiments, the method is further defined as a method of manufacturing food and/or feed. The invention also provides food or feed made by the method.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
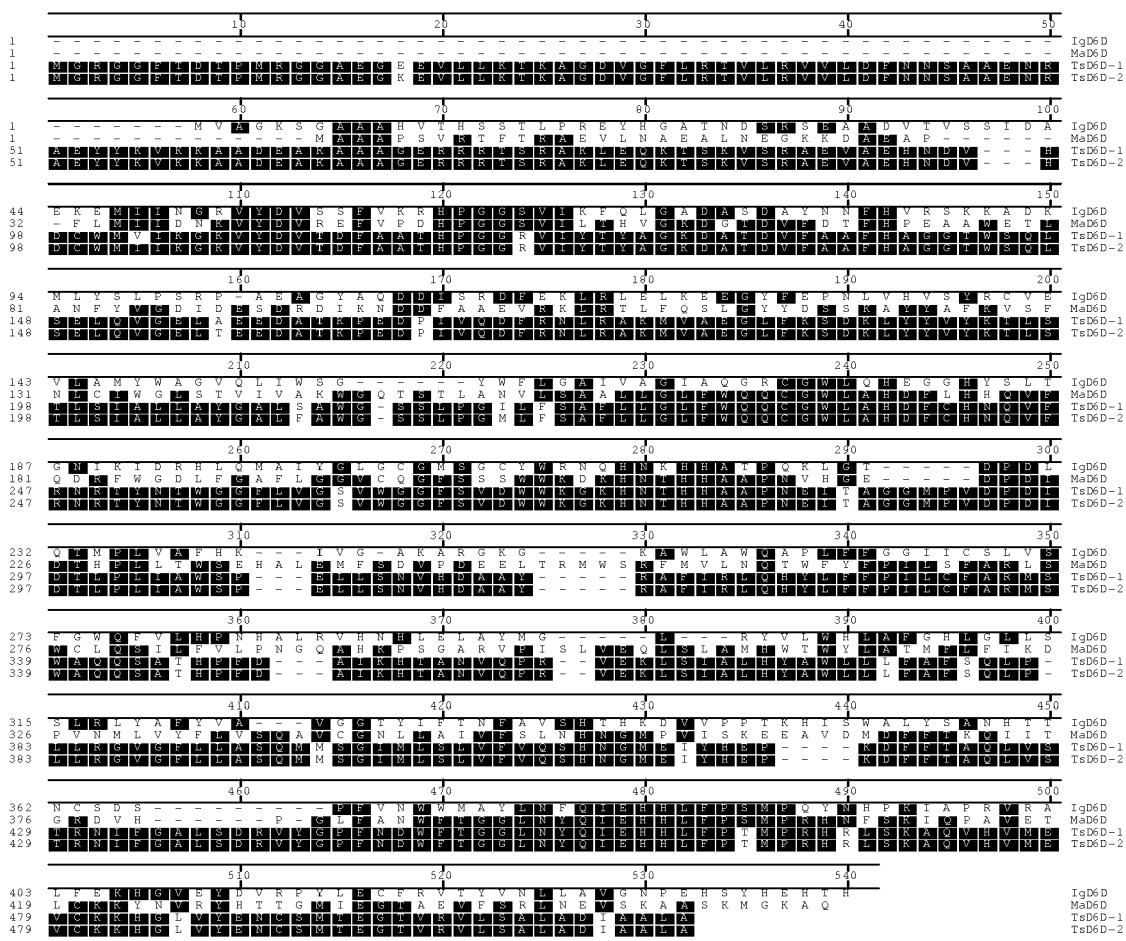
FIG. 1 shows an amino acid alignment of *Tetraselmis suecica* Δ6 desaturases TsD6D-1 and TsD6D-2 (SEQ ID NOs: 2 and 4), *Isochysis galba* Ig6D-1 (SEQ ID NO: 11) and *Mortierella alpina* D6D (SEQ ID NO:12).

The invention overcomes the limitations of the prior art by providing methods and compositions for creation of plants with improved PUFA content. The modification of fatty acid content of an organism such as a plant presents many advantages, including improved nutrition and health benefits. Modification of fatty acid content can be used to achieve beneficial levels or profiles of desired PUFA's in plants, plant parts, and plant products, including plant seed oils. For example, when the desired PUFA's are produced in the seed tissue of a plant, the oil may be isolated from the seeds typically resulting in an oil high in desired PUFAs or an oil having a desired fatty acid content or profile, which may in turn be used to provide beneficial characteristics in food stuffs and other products.

Various aspects of the invention include methods and compositions for modification of PUFA content of a cell, for example, modification of the PUFA content of a plant cell(s). Compositions related to the invention include novel isolated polynucleotide sequences, polynucleotide constructs and plants and/or plant parts transformed by polynucleotides of the invention. The isolated polynucleotide may encode a *Tetraselmis suecica* Δ6-desaturase. Host cells may be manipulated to express a polynucleotide encoding a delta 6 desaturase polypeptide(s) which catalyze(s) desaturation of a fatty acid(s).

The following definitions are provided as an aid to understanding this invention. The phrases "DNA sequence," "nucleic acid sequence," "nucleic acid molecule," "polynucleotide" and "nucleic acid segment" refer to a physical structure comprising an orderly arrangement of nucleotides. The DNA segment, sequence, or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The phrases "coding sequence," "coding region," "structural sequence," and "structural nucleic acid sequence" refer to all or a segment of a DNA sequence, nucleic acid sequence, nucleic acid molecule in which the nucleotides are arranged in a series of triplets that each form a codon. Each codon encodes a specific amino acid. Thus, the coding sequence, coding region, structural sequence, and structural nucleic acid sequence encode a series of amino acids forming a protein, polypeptide, or peptide sequence. The coding sequence, coding region, structural sequence, and structural nucleic acid sequence may be contained within a larger nucleic acid molecule, vector, or the like. In addition, the arrangement of nucleotides in these sequences may be depicted in the form of a sequence listing, figure, table, electronic medium, or the like.

The term "cDNA" refers to a double-stranded DNA that is complementary to and derived from mRNA.

"Desaturase" refers to a polypeptide that can desaturate or catalyze formation of a double bond between consecutive carbons of one or more fatty acids to produce a mono- or poly-unsaturated fatty acid or a precursor thereof. Of particular interest are polypeptides that can catalyze the conversion of OA to LA, LA to ALA, or ALA to SDA, which includes enzymes which desaturate at the 12, 15, or 6 positions. Considerations for choosing a specific polypeptide having desaturase activity include, but are not limited to, the pH optimum of the polypeptide, whether the polypeptide is a rate limiting enzyme or a component thereof, whether the desaturase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s).

"Expression" refers to the process by which a gene's coded information is converted into structures present and operating in the cell. Expressed genes include those that are transcribed into RNA and then translated into protein and those that are transcribed into RNA but not translated into protein (e.g., transfer RNA and ribosomal RNA).

As used herein, "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous" gene refers to a native gene in its natural location in the genome of an organism. An "exogenous" gene or "transgene" refer to a gene that has been introduced into the genome by a transformation procedure. A transgene includes genomic DNA introduced by a transformation procedure (e.g., a genomic DNA linked to its active promoter).

"Heterologous" refers to the relationship between 2 or more nucleic acid or protein sequences that are derived from different sources. For example, a promoter is heterologous with respect to a coding sequence if such a combination is not normally found in nature. In addition, a particular nucleic acid sequence may be "heterologous" with respect to a cell or organism into which it is inserted if it does not naturally occur in that particular cell or organism.

"Sequence homology" refers to the level of similarity between 2 or more nucleic acid or amino acid sequences in terms of percent of positional identity. The term homology is also used to refer to the concept of similar functional properties among different nucleic acids or proteins.

"Hybridization" refers to the ability of a first strand of nucleic acid to join with a second strand via hydrogen bond base pairing when the nucleic acid strands have sufficient sequence complementarity. As used herein, a nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Thus 2 nucleic acid strands are said to have sufficient complementarity when they can hybridize to one another with sufficient stability to permit them to remain annealed to one another under appropriate conditions.

The phrase "isolated" means having been removed from its natural environment, regardless of its eventual disposition. For example, a nucleic acid sequence "isolated" from rice, such as by cloning from a rice cell, remains "isolated" when it is inserted into the genome of a corn cell.

The phrase "operably linked" refers to the spatial arrangement of two or more nucleic acid regions or nucleic acid sequences so that they exert their appropriate effects with respect to each other. For example, a promoter region may be positioned relative to a nucleic acid sequence such that transcription of the nucleic acid sequence is directed by the promoter region. The promoter region and the nucleic acid sequence are "operably linked."

"Upstream" and "downstream" are positional terms used with reference to the location of a nucleotide sequence and the direction of transcription or translation of coding sequences, which normally proceeds in the 5' to 3' direction.

The terms "promoter" or "promoter region" refer to a nucleic acid sequence, usually found upstream (5') to a coding sequence, capable of directing transcription of a nucleic acid sequence into an RNA molecule. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, and the like. The activity or strength of a promoter may be measured in terms of the amounts of RNA it produces, or the amount of protein accumulation in a cell or tissue, relative to a second promoter that is similarly measured.

The phrase "3' non-coding sequences" refers to nucleotide sequences located downstream of a coding sequence and include polyadenylation recognition sequences and other sequences encoding regulatory signals capable of affecting mRNA processing or gene expression. These are commonly referred to as 3'-untranslated regions or 3'-UTRs. The polyadenylation signal is usually characterized by affecting the addition of polyadenylic acid tracts to the 3' end of the mRNA precursor. The use of different 3' non-coding sequences is exemplified by Ingelbrecht et al. (1989).

"Translation leader sequence" or "5'-untranslated region" or "5'-UTR" all refer to a nucleotide sequence located between the promoter sequence of a gene and the coding sequence. The 5'-UTR is present in the fully processed mRNA upstream of the translation start sequence. The 5'-UTR may affect processing of the primary transcript to mRNA, mRNA stability or translation efficiency. Examples of translation leader sequences have been described (Turner and Foster, 1995).

"RNA transcript" refers to the product resulting from RNA polymerase-catalyzed transcription of a DNA sequence. When the RNA transcript is a perfect complementary copy of the DNA sequence, it is referred to as the primary transcript. An RNA sequence derived from posttranscriptional processing of the primary transcript is referred to as the mature RNA. "Messenger RNA" (mRNA) refers to the RNA that is without introns and that can be translated into polypeptide by the cell.

"DNA construct" refers to the heterologous genetic elements operably linked to each other making up a recombinant DNA molecule and may comprise elements that provide expression of a DNA polynucleotide molecule in a host cell and elements that provide maintenance of the construct. A plant expression cassette comprises the operable linkage of genetic elements that when transferred into a plant cell provides expression of a desirable gene product.

"Recombinant vector" refers to any agent by or in which a nucleic acid of interest is amplified, expressed, or stored, such as a plasmid, cosmid, virus, autonomously replicating sequence, phage, or linear single-stranded, circular single-stranded, linear double-stranded, or circular double-stranded DNA or RNA nucleotide sequence. The recombinant vector may be synthesized or derived from any source and is capable of genomic integration or autonomous replication.

"Regulatory sequence" refers to a nucleotide sequence located upstream (5'), within, or downstream (3') with respect to a coding sequence, or an intron, whose presence or absence affects transcription and expression of the coding sequence "Substantially homologous" refers to two sequences that are at least about 90% identical in sequence, as measured by the CLUSTAL W algorithm in, for example DNAStar (DNAStar, Madison, Wis.).

"Substantially purified" refers to a molecule separated from substantially all other molecules normally associated with it in its native state. More preferably, a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The phrase "substantially purified" is not intended to encompass molecules present in their native state. Preferably, the nucleic acid molecules and polypeptides of this invention are substantially purified.

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, a "transgenic plant" is a plant having stably introduced into its genome, for example, the nuclear or plastid genomes, an exogenous nucleic acid.

The term "isogenic" as a comparative term between plants or plant lines having or lacking a transgene means plants or lines having the same or similar genetic backgrounds, with the exception of the transgene in question. For example, so-called sister lines representing phenotypically similar or identical selections from the same parent F2 population are considered to be "isogenic." When the progeny of a stable transformant plant are crossed and backcrossed with the plants of the untransformed parent line for 3 to 6 generations (or more) using the untransformed parent as the recurrent parent while selecting for type (genotype by molecular marker analysis, phenotype by field observation, or both) and for the transgene, the resulting transgenic line is considered to be highly "isogenic" to its untransformed parent line.

The terms "seeds" "kernels" and "grain" are understood to be equivalent in meaning. The term kernel is frequently used in describing the seed of a corn or rice plant. In all plants the seed is the mature ovule consisting of a seed coat, embryo, aleurone, and an endosperm.

Nucleic Acids Encoding Delta 6 Desaturases

The invention provides, in one embodiment, novel nucleic acids encoding delta 6 desaturases from *Tetraselmis suecica*, a motile green flagellate alga. In a particular embodiment, the nucleic acids are isolated from *Tetraselmis suecica* strain CCMP904 (available from CCMP; Center for Culture of Marine Phytoplankton; West Boothbay Harbor, Me., USA). In certain embodiments, the nucleic acids comprise SEQ ID NOs:1 or 3. The invention also provides methods of using such nucleic acids, including SEQ ID NOs:1 and 3. In one embodiment, these nucleic acid molecules are used in the context of this invention for altering the oil composition of a seed from a plant.

Such nucleic acid can be amplified using cDNA, mRNA or genomic DNA as a template and appropriate oligonucleotide primers according to standard PCR™ amplification techniques. Alternatively, they can be synthesized using standard synthetic techniques, such as an automated DNA synthesizer. Polynucleotides encoding desired delta 6 desaturases can be identified in a variety of ways. As an example, a source of the desired delta 6 desaturases, for example a library from *Tetraselmis*, is screened with detectable enzymatically- or chemically-synthesized probes, which can be made from DNA, RNA, or non-naturally occurring nucleotides, or mixtures thereof. Probes may be enzymatically synthesized from polynucleotides of known delta 6 desaturases for normal or reduced-stringency hybridization methods. Oligonucleotide probes also can be used to screen sources and can be based on sequences of known delta 6 desaturases, including sequences conserved among known delta 6 desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR™ from reverse transcribed mRNA from a known or suspected source; the PCR™ product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

If desired, the sequences of nucleic acids that code for delta 6 desaturases can be modified without changing the resulting amino acid sequence of the expressed protein so that the sequences are more amenable to expression in plant hosts. A coding sequence can be an artificial DNA. An artificial DNA, as used herein means a DNA polynucleotide molecule that is non-naturally occurring. Artificial DNA molecules can be designed by a variety of methods, such as, methods known in the art that are based upon substituting the codon(s) of a first polynucleotide to create an equivalent, or even an improved, second-generation artificial polynucleotide, where this new artificial polynucleotide is useful for enhanced expression in transgenic plants. The design aspect often employs a codon usage table produced by compiling the frequency of occurrence of codons in a collection of coding sequences isolated from a plant, plant type, family or genus. Other design aspects include reducing the occurrence of polyadenylation signals, intron splice sites, or long AT or GC stretches of sequence (U.S. Pat. No. 5,500,365). Full length coding sequences or fragments thereof can be made of artificial DNA using methods known to those skilled in the art. Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

The inventors have isolated DNA sequences from *Tetraselmis suecica* that produce polypeptides with delta 6 desaturase activity. The sequences encoding the delta 6 desaturases may be expressed in transgenic plants, microorganisms or animals to modify fatty acid content. Other polynucleotides which are substantially identical to the delta 6 desaturase polynucleotides provided herein, or which encode polypeptides which are substantially identical to the delta 6 desaturase polypeptides, also can be used. "Substantially identical" refers to an amino acid sequence or nucleic acid sequence exhibiting in order of increasing preference at least 75%, 80%, 82%, 85%, 87%, 90%, 92%, 95%, 98 or 99% identity to the delta 6 desaturase polypeptide sequence in SEQ ID NO:2, SEQ ID NO:4 or sequences encoding these polypeptides. Polypeptide or polynucleotide comparisons may be carried out using sequence analysis software, for example, the Sequence Analysis software package of the GCG Wisconsin Package (Accelrys, San Diego, Calif.) and MEGAlign (DNAStar, Inc., 1228 S. Park St., Madison, Wis. 53715). Such software matches similar sequences by assigning degrees of similarity or identity.

DNA Constructs

The invention provides DNA constructs comprising a heterologous promoter operably linked to a nucleic acid described herein. The selection of promoters, e.g., promoters that may be described as strongly expressed, weakly expressed, inducibly expressed, tissue-enhanced expressed (i.e., specifically or preferentially expressed in a tissue), organ-enhanced expressed (i.e., specifically or preferentially expressed in an organ) and developmentally-enhanced expressed (i.e., specifically or preferentially expressed during a particular stage(s) of development), is within the skill in the art. Similarly, the combining of a nucleic acid molecule as described above with a promoter is also within the skill in the art (see, e.g., Sambrook et al., 2001, 1989).

Promoters for use with the invention include, but are not limited to, promoters that function in bacteria, bacteriophages, fungi or plant cells. Useful promoters for bacterial expression are the lacZ, Sp6, T7, T5 or *E. coli* glgC promoters. Useful promoters for fungi include *Saccharomyces cerevisiae* gal1 (West et al., 1984), *Saccharomyces pombe* nmt1 (Maundrell, 1990), *Neurospora crassa* ccg-1 (Freitag and Selker, 2005) and *Pichia methanolica* AUG1 (Invitrogen). Useful promoters for plants cells include the gamma zein Z27 promoter (see, for example, Prem Das et al., 1991), L3 oleosin promoter (U.S. Pat. No. 6,433,252, Kriz et al.), barley PER1 promoter (Stacey et al., 1996), CaMV 35S promoter (U.S. Pat. No. 5,530,196 (Fraley et al.)), nos promoter (Ebert et al., 1987), rice actin promoter (U.S. Pat. No. 5,641,876), and PEPCase promoter (Hudspeth et al., 1989). The Figwort Mosaic Virus (FMV) promoter (U.S. Pat. No. 6,051,753 (Comai et al.)), arcelin, tomato E8, patatin, ubiquitin, mannopine synthase (mas) and tubulin promoters are other examples of useful promoters.

There are a wide variety of plant promoter sequences which may be used to drive tissue-specific expression of polynucleotides encoding delta 6 desaturases and other desaturases in transgenic plants. Indeed, in particular embodiments of the invention, the promoter used is a seed specific promoter. Examples of such promoters include the 5' regulatory regions from such genes as napin (Kridl et al., 1991), phaseolin (Bustos, et al., 1989), soybean a' subunit of β-conglycinin (P-Gm7S alpha', see for example, Chen et al., 1986), *Vicia faba* USP (P-Vf.Usp, see for example, SEQ ID NO:1, 2, and 3, U.S. Patent Publication 20030229918), the globulin promoter (see for example Belanger and Kriz, 1991), and soybean alpha subunit of β-conglycinin (7S alpha) (U.S. Patent Publication 20030093828, incorporated by reference).

Other seed-expression enhanced promoters known to function in maize and in other plants include the promoters for the following genes: Waxy (granule bound starch synthase), Brittle and Shrunken 2 (ADP glucose pyrophosphorylase), Shrunken 1 (sucrose synthase), branching enzymes I and II, starch synthases, debranching enzymes, oleosins, glutelins, and Bet1l (basal endosperm transfer layer). Other promoters useful in the practice of the invention that are known by one of skill in the art are also contemplated by the invention.

Moreover, transcription enhancers or duplications of enhancers can be used to increase expression from a particular promoter. Examples of such enhancers include, but are not limited to the Adh intron1 (Callis et al., 1987), a rice actin intron (McElroy et al., 1991, U.S. Pat. No. 5,641,876), sucrose synthase intron (Vasil et al., 1989), a maize HSP70 intron (also referred to as Zm.DnaK) (U.S. Pat. No. 5,424,412, Brown et al.) a TMV omega element (Gallie et al., 1999), the CaMV 35S enhancer (U.S. Pat. Nos. 5,359,142 & 5,196,525, McPherson et al.) or an octopine synthase enhancer (U.S. Pat. No. 5,290,924, Last et al.). As the DNA sequence between the transcription initiation site and the start of the coding sequence, i.e. the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, 1987). The choice of such sequences is at the discretion of those of skill in the art.

DNA constructs of the invention may include a sequence near the 3' end of the cassette that acts as a signal to terminate transcription from a heterologous nucleic acid and that directs polyadenylation of the resultant mRNA. These are commonly referred to as 3' untranslated regions or 3' UTRs. Some 3' elements that can act as transcription termination signals include those from the nopaline synthase gene (nos) of *Agrobacterium tumefaciens* (Bevan et al., 1983), a napin 3' untranslated region (Kridl et al., 1991), a globulin 3' untranslated region (Belanger and Kriz, 1991), 3' untranslated region from the Adr12 gene of soybean (auxin down regulated) (Wang et al., PCT Publication WO200250295) or one from a zein gene, such as Z27 (Lopes et al., 1995). Other 3' regulatory elements known to the art also can be used in the vectors of the invention.

A nucleic acid molecule as described herein can be cloned into any suitable vector and can be used to transform or transfect any suitable host. The selection of vectors and methods to construct them are commonly known to the art and are described in general technical references (see, in general, Recombinant DNA Part D, 1987). The vector will preferably comprise regulatory sequences, such as transcription and translation initiation and termination codons, which are specific to the type of host (e.g., bacterium, fungus, or plant) into which the vector is to be introduced, as appropriate and taking into consideration whether the vector is DNA or RNA.

Vectors that are circular or linear can be prepared to contain an entire nucleic acid sequence as described above or a portion thereof ligated to a replication system functional in a prokaryotic or eukaryotic host cell. Replication systems can be derived from ColE1, 2 mμ plasmid, λ phage, f1 filamentous phage, *Agrobacterium* species (e.g., *A. tumefaciens* and *A. rhizogenes*), and the like.

In addition to the replication system and the inserted nucleic acid sequence, the vector can include one or more marker genes that allow for selection of transformed or transfected hosts. Marker genes include biocide resistance, such as resistance to antibiotics, heavy metals, herbicides, etc., complementation in an auxotrophic host to provide prototrophy, and the like.

The invention provides host cells comprising a nucleic acid molecule described herein, optionally in the form of a vector. Suitable hosts include plant, bacterial and fungal cells, including *Escherichia coli, Bacillus subtilis, Agrobacterium tumefaciens, Saccharomyces cerevisiae* and *Neurospora crassa. E. coli* hosts include TB-1, TG-2, DH5α, XL-Blue MRF' (Stratagene, Austin, Tex.), SA2821, Y1090 and TG02. Plant cells include, but not limited to, soybean, *Brassica campestris*, canola, oilseed rape, rapeseed, crambe, mustard, castor bean, peanut, sesame, cottonseed, linseed, safflower, oil palm, flax, sunflower, alfalfa, corn, wheat, barley, oats, rye, millet, sorghum, and rice.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Expression in a host cell may involve fermentation techniques known to one skilled in the art. The fermented host cell may be a prokaryote, such as *Escherichia coli*, or a eukaryote, such as the yeast *Saccharomyces cerevisiae* or *Neurospora crassa*, a filamentous fungi. Examples of production of PUFA by fermentation include *Mortierella* (U.S. Pat. No. 6,319,698) and *Thraustrochytriales* (U.S. Pat. No. 6,451,567).

It is contemplated that more than one gene may be introduced and propagated in a host cell through the use of episomal or integrated expression vectors. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced polynucleotides are expressed at the necessary levels to provide for synthesis of the desired products.

Polypeptides

The invention provides delta 6 desaturases encoded by nucleic acid molecules described herein. Delta 6 desaturases are enzymes that can desaturate or catalyze formation of a double bond between consecutive carbons at the 6 position of one or more fatty acids to produce a mono- or poly-unsaturated fatty acid or a precursor thereof. The polypeptide can comprise D-amino acids, L-amino acids or a mixture of D- and L-amino acids.

Alterations of the native amino acid sequence to produce variant polypeptides can be prepared by a variety of means known to those ordinarily skilled in the art. For instance, amino acid substitutions can be conveniently introduced into the polypeptides by changing the sequence of the nucleic acid molecule at the time of synthesis. Site-specific mutations can also be introduced by ligating into an expression vector a synthesized oligonucleotide comprising the modified sequence. Alternately, oligonucleotide-directed, site-specific mutagenesis procedures can be used, such as disclosed in Walder et al. (1986); Bauer et al. (1985); and U.S. Pat. Nos. 4,518,584 and 4,737,462.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids is relatively hydrophobic when incorporated into a polypeptide, but glycines lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the ordinarily skilled artisan can readily group synthetic amino acids with naturally-occurring amino acids.

If desired, the polypeptides can be modified, for instance, by glycosylation, amidation, carboxylation, or phosphorylation, or by the creation of acid addition salts, amides, esters, in particular C-terminal esters, and N-acyl derivatives of the polypeptides of the invention. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the polypeptides, or at the N- or C-terminus. Desirably, such modifications and conjugations do not adversely affect the activity of the polypeptides (and variants thereof). While such modifications and conjugations can have greater or lesser activity, the activity desirably is not negated and is characteristic of the unaltered polypeptide.

The polypeptides (and fragments, variants and fusion proteins) can be prepared by any of a number of conventional techniques. The polypeptide can be isolated or substantially purified from a naturally occurring source or from a recombinant source. For instance, in the case of recombinant proteins, a DNA fragment encoding a desired protein can be subcloned into an appropriate vector using well-known molecular genetic techniques (see, e.g., Maniatis et al., 1989) and other references cited herein under "EXAMPLES"). The fragment can be transcribed and the protein subsequently translated in vitro. Commercially available kits also can be employed (e.g., such as manufactured by Clontech, Mountain View, Calif.; Amersham Life Sciences, Inc., Arlington Heights, Ill.; Invitrogen, Carlsbad, Calif. and the like). The polymerase chain reaction optionally can be employed in the manipulation of nucleic acids.

Polypeptides can be synthesized using an automated peptide synthesizer in accordance with methods known in the art. Alternately, the polypeptide (and fragments, variants, and fusion proteins) can be synthesized using standard peptide synthesizing techniques well-known to those of ordinary skill in the art (e.g., as summarized in Bodanszky, 1984). In particular, the polypeptide can be synthesized using the procedure of solid-phase synthesis (see, e.g., Merrifield, 1963; Barany et al., 1987 and U.S. Pat. No. 5,424,398). If desired, this can be done using an automated peptide synthesizer. Removal of the t-butyloxycarbonyl (t-BOC) or 9-fluorenyl-methyloxycarbonyl (Fmoc) amino acid blocking groups and separation of the protein from the resin can be accomplished by, for example, acid treatment at reduced temperature. The polypeptide-containing mixture then can be extracted, for instance, with diethyl ether, to remove non-peptidic organic compounds, and the synthesized protein can be extracted from the resin powder (e.g., with about 25% w/v acetic acid). Following the synthesis of the polypeptide, further purification (e.g., using HPLC) optionally can be done in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation, or through genetic means known to the art. In this regard, this invention also provides a fusion protein comprising the polypeptide (or fragment thereof) or variant thereof and one or more other polypeptides/protein(s) having any desired properties or effector functions.

Assays for the production and identification of specific proteins are based on various physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches can be used to achieve even greater specificity such as western blotting in which antibodies are used to locate individual gene products that have been separated by electrophoretic techniques. Additional techniques can be used to absolutely confirm the identity of the product of interest such as evaluation by amino acid sequencing following purification. Although these are among the most common, other procedures can also be used.

Assay procedures can identify the expression of proteins by their functionality, particularly where the expressed protein is an enzyme capable of catalyzing chemical reactions involving specific substrates and products. For example, in plant extracts these reactions can be measured by providing and quantifying the loss of substrates or the generation of products of the reactions by physical and/or chemical procedures.

In many cases, the expression of a gene product is determined by evaluating the phenotypic results of its expression. Such evaluations may be simply as visual observations, or may involve assays. Such assays can take many forms, such as analyzing changes in the chemical composition, morphology, or physiological properties of the plant. Chemical composition may be altered by expression of genes encoding enzymes or storage proteins that change amino acid composition and these changes can be detected by amino acid analysis, or by enzymes that change starch quantity, which can be analyzed by near infrared reflectance spectrometry or by enzymes that change oil composition, which can be detected by gas chromatography. Morphological changes may include greater stature or thicker stalks.

The nucleic acid molecules, DNA constructs and polypeptides of this invention can be used in agricultural methods and various screening assays. For example, a nucleic acid molecule can be used to express a delta 6 desaturase via a vector in a host cell, to detect mRNA transcripts encoding delta 6 desaturases in a biological sample, to detect a genetic alteration in a gene encoding delta 6 desaturase via a Southern blot, to suppress delta 6 desaturases, or to up-regulate delta 6 desaturases. The polypeptides can be used to compensate for deficiencies in delta 6 desaturases or for the presence of a mutated delta 6 desaturases having reduced or no activity in a plant, or to treat excessive levels of substrates, whether direct or indirect, for delta 6 desaturases in a plant. Alternatively, the polypeptides can be used to screen agents for the ability to modulate their activity. The antibodies can be used to detect and isolate the respective polypeptides as well as decrease the availability of such polypeptides in vivo.

Plant Transformation

In a preferred embodiment of the invention, a transgenic plant expressing the desired protein or proteins is produced. Various methods for the introduction of a desired polynucleotide sequence encoding the desired protein into plant cells are known to the art, including: (1) physical methods such as microinjection, electroporation, and microparticle-mediated delivery (biolistics or gene gun technology); (2) virus-mediated delivery; and (3) *Agrobacterium*-mediated transformation.

The most commonly used methods for transformation of plant cells are the *Agrobacterium*-mediated DNA transfer process and the biolistics or microprojectile microparticle bombardment mediated process. Typically, nuclear transformation is desired but where it is desirable to specifically transform plastids, such as chloroplasts or amyloplasts, plant plastids may be transformed utilizing a microparticle-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species, as further elaborated, for example, in U.S. Pat. No. 6,265,638 to Bidney et al., the disclosures of which are hereby incorporated herein by reference.

*Agrobacterium*-mediated genetic transformation of plants involves several steps. The first step, in which the virulent *Agrobacterium* and plant cells are first brought into contact with each other, is generally called "inoculation". Inoculation is preferably accompanied by some method of injury to some of the plant cells, which releases plant cellular constituents, such as coumaryl alcohol, sinapinate (which is reduced to acetosyringone), sinapyl alcohol, and coniferyl alcohol, that activate virulence factors in the *Agrobacterium*. Following the inoculation, the Agrobacterium and plant cells/tissues are permitted to grow together for a period of several hours to several days or more under conditions suitable for growth and T-DNA transfer. This step is termed "co-culture". Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microparticle bombardment (U.S. Pat. No. 5,550,318 (Adams et al.); U.S. Pat. No. 5,538,880 (Lundquist et. al.), U.S. Pat. No. 5,610,042 (Chang et al.); and PCT WO 95/06128 (Adams et al.); each of which is specifically incorporated herein by reference in its entirety), microscopic particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microparticle bombardment techniques are widely applicable, and may be used to transform virtually any plant species. Examples of species that have been transformed by microparticle bombardment include monocot species such as maize (International Publication No. WO 95/06128 (Adams et al.)), barley, wheat (U.S. Pat. No. 5,563,055 (Townsend et al.)) incorporated herein by reference in its entirety), rice, oat, rye, sugarcane, and sorghum; as well as a number of dicots including tobacco, soybean (U.S. Pat. No. 5,322,783 (Tomes et al.)), incorporated herein by reference in its entirety), sunflower, peanut, cotton, tomato, and legumes in general (U.S. Pat. No. 5,563,055 (Townsend et al.)) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scoreable marker would include but are not limited to β-glucuronidase (GUS), green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No. 5,633,435 (Barry, et al.), and U.S. Pat. No. 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (crtI) described in Misawa et al. (1993); Misawa et al. (1994) for norflurazon tolerance; a polynucleotide molecule encoding acetohydroxyacid synthase (AHAS, aka ALS) described in Sathasiivan et al. (1990) for tolerance to sulfonylurea herbicides; and both the pat gene described in Wohlleben et al., (1988) and bar gene described in DeBlock et al. (1987), each of which provides glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

This invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves. The Tomes et al. '783 patent, cited above, describes a method of treatment with a cytokinin followed by incubation for a period sufficient to permit undifferentiated cells in cotyledonary node tissue to differentiate into meristematic cells and to permit the cells to enter the phases between the G1 and division phases of development, which is stated to improve susceptibility for transformation.

Any suitable plant culture medium can be used. Suitable media include but are not limited to MS-based media (Murashige and Skoog, 1962) or N6-based media (Chu et al., 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

After a DNA construct is stably incorporated in transgenic plants and confirmed to be operable, it can be introduced into other plants of the same or another sexually compatible species by sexual crossing. Any of a number of standard breeding techniques can be used, depending upon the species to be crossed. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Backcrossing is herein defined as the process including the steps of: (a) crossing a plant of a first genotype containing a desired gene, DNA sequence or element to a plant of a second genotype lacking said desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Seeds, Meal, Oil and Products Comprising Seeds, Meal and Oil

This invention also provides a container of over about 1000, more preferably about 20,000, and even more preferably about 40,000 seeds where over about 10%, more preferably about 25%, more preferably about 50%, and even more preferably about 75% or more preferably about 90% of the seeds are seeds derived from a plant of this invention.

This invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of this invention.

Any of the plants or parts thereof of this invention may be harvested and, optionally, processed to produce a feed, meal, or oil preparation. A particularly preferred plant part for this purpose is harvested grain, but other plant parts can be harvested and used for stover or silage. Methods to produce feed, meal, and oil preparations are known in the art. See, for example, U.S. Pat. Nos. 4,957,748; 5,100,679; 5,219,596; 5,936,069; 6,005,076; 6,146,669; and 6,156,227. The grain or meal of this invention may be blended with other grains or meals.

The invention provides an oil composition extracted from corn seed having a GLA content of from about 5% to about 26% by weight of total fatty acids and further comprising and SDA content from about 3% to about 13%. The invention is also embodied by an oil composition extracted from corn seed comprising a GLA content of at least 3% by weight of total fatty acids and an SDA content of at least 3% by weight of total fatty acids, wherein the ratio of GLA/SDA is between about 1.3 and about 3.7. The invention also provides an oil composition extracted from soybean seed having a GLA content from about 9% to about 51% by weight of total fatty acids and may further comprise an SDA content of from about 0.5% to about 10% by weight of total fatty acids. The invention is also embodied by an oil composition extracted from soybean seed comprising a GLA content of at least 1% by weight of total fatty acids and an SDA content of at least 1% by weight of total fatty acids, wherein the ratio of GLA/SDA is between about 2.8 and about 18.3.

Methods

The present invention provides a method for providing transgenic plants with an increased content of GLA or SDA. This method may include, for example, introducing DNA encoding a delta 6 desaturase and optionally at least one additional desaturase into plant cells and regenerating plants with increased GLA or SDA content from the transgenic cells.

More specifically, the invention provides a method of producing food or feed, comprising the steps of (a) obtaining the transgenic plant of the invention; and (b) producing the food or feed. The food or feed may be oil, silage, meal, grain, starch, flour or protein. The food or feed composition is defined as comprising a detectable polynucleotide sequence or detectable polypeptide provided by the invention. Additionally, the invention provides animal feed and human food compositions comprising GLA or SDA.

For dietary supplementation, the purified PUFAs, transformed plants or plant parts, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

As used herein, "edible composition" is defined as compositions which may be ingested by a mammal such as foodstuffs, nutritional substances and pharmaceutical compositions. As used herein "foodstuffs" refer to substances that can be used or prepared for use as food for a mammal and include substances that may be used in the preparation of food (such as frying oils) or food additives. For example, foodstuffs include animals used for human consumption or any product therefrom, such as, for example, eggs. Typical foodstuffs include but are not limited to beverages, (e.g., soft drinks, carbonated beverages, ready to mix beverages), infant formula, infused foods (e.g. fruits and vegetables), sauces, condiments, salad dressings, fruit juices, syrups, desserts (e.g., puddings, gelatin, icings and fillings, baked goods and frozen desserts such as ice creams and sherbets), soft frozen products (e.g., soft frozen creams, soft frozen ice creams and yogurts, soft frozen toppings such as dairy or non-dairy whipped toppings), oils and emulsified products (e.g., shortening, margarine, mayonnaise, butter, cooking oil, and salad dressings) and intermediate moisture foods (e.g., rice and dog foods).

Furthermore, edible compositions described herein can also be ingested as an additive or supplement contained in foods and drinks. These can be formulated together with a nutritional substance such as various vitamins and minerals and incorporated into substantially liquid compositions such as nutrient drinks, soymilks and soups; substantially solid compositions; and gelatins or used in the form of a powder to be incorporated into various foods. The content of the effective ingredient in such a functional or health food can be similar to the dose contained in a typical pharmaceutical agent.

The purified PUFAs, transformed plants or plant parts may also be incorporated into animal, particularly livestock, feed. In this way, the animals themselves may benefit from a PUFA rich diet, while human consumers of food products produced from such livestock may benefit as well.

For pharmaceutical use (human or veterinary), the compositions may generally be administered orally but can be administered by any route by which they may be successfully absorbed, e.g., parenterally (i.e. subcutaneously, intramuscularly or intravenously), rectally, vaginally or topically, for example, as a skin ointment or lotion. The PUFAs, transformed plants or plant parts of the present invention may be administered alone or in combination with a pharmaceutically acceptable carrier or excipient. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Cloning of *Tetraselmis suecica* Δ6 Desaturase Sequences

Cloning of the *Tetraselmis suecica* Δ6 desaturase (TsD6D) was achieved by PCR amplification of a partial internal genomic DNA region using degenerate oligonucleotides, followed by RACE library screening. Genomic DNA was isolated from *T. suecica* strain CCMP904 (CCMP, West Boothbay Harbor, Me., USA) using DNasol (InVitrogen, Carlsbad, Calif.). A 578 bp internal region was amplified by PCR using the degenerate oligonucleotide primers D6DegF2: 5'-TG-GTGGAARRMSAAGCAYAAC-3' (SEQ ID NO:5) and D6DegR3: 5'-ARDCCWCCVBDRAACCARTY-3' (SEQ ID NO:6). These primers were designed using DNA sequence alignments of related Δ6 desaturases. The resulting PCR fragment was ligated into the pCR2.1-TOPO (Invitrogen), giving the plasmid pMON67050. After sequencing, the cloned insert was found to contain the conserved amino acid sequence QXXHH (SEQ ID NO:22), which is found in all front-end desaturases (Napier et al., 1997, Napier et al., 2003, Sperling and Heinz, 2001). Examples of front-end desaturases include the Δ4, Δ5, and Δ6 fatty acid desaturases, in addition to the sphingolipid Δ8 desaturases. This genomic sequence allowed for the design of gene-specific primers so that a full-length putative Δ6 desaturase cDNA could be cloned.

Total RNA was isolated from *T. suecica* cells by a modified CTAB procedure (Jones et al., 1995) and the RNA was used to generate a GeneRacer™ library following the manufacturer's instructions (Invitrogen). A 5' RACE reaction using the gene specific primer, Phy D6 R2: 5'-AGTAGCCAGGCAT-AGTGCAGCGCAAT-3' (SEQ ID NO:7) and the GeneRacer 5' Primer: 5'-CGACTGGAGCACGAGGACACTGA-3' (Invitrogen; (SEQ ID NO:23)) yielded a 1264 bp fragment that overlapped with pMON67050 by 310 bp. A 3' RACE reaction using the gene-specific primer D6DegF3: 5'-TTCAACGAT-TGGTTCACGGGTGGC-3' (SEQ ID NO:8) and the GeneRacer 3' Primer: 5'-GCTGTCAACGATACGCTACGTAACG-3' (Invitrogen (SEQ ID NO:24)) yielded a 405 bp fragment that overlapped by 56 bp with the 5' RACE product to give a combined virtual fragment with an open reading frame (ORF) of 1529 nucleotides. The predicted amino acid sequence from the ORF contained conserved sequences that are diagnostic for a Δ6 fatty acid desaturase including an N-terminal cytochrome $b_5$ domain which is found in all front-end desaturases (Napier et al., 2003) and three conserved histidine boxes that are characteristic of all membrane-bound desaturases (Shanklin et al., 1994). A distinguishing feature found in all front-end desaturases including the putative TsD6D herein is that the third histidine box contains a glutamine residue in the first position (Q-x-x-H-H) instead of a histidine (Napier et al., 1997, Napier et al., 2003, Sperling and Heinz, 2001).

Using the *T. suecica* RACE sequences described above, specific oligonucleotide primers were designed to amplify the complete ORF for the putative TsD6D. The first primer (TsD6D-F1: 5'-AACATGGGCAGGGGTGGGTTTACTG-3' (SEQ ID NO:9)) added a yeast Kozak sequence 5' of the ATG start site and the reverse primer (TsD6D-R1: 5'-CTAAGCAAGTGCCGCGATGTCCG-3' (SEQ ID NO:10)) added a stop codon to the 3' end of the amplified product. These primers were used to generate a 1536 bp fragment by PCR amplification from the RACE library that was ligated into the yeast expression vector pYES2.1/V5-His-TOPO (Invitrogen). Two distinct versions of the full-length ORFs were identified which differed by 22 nucleotides and 5 amino acids. The nucleic acid sequences of the two putative *T. suecica* Δ6 fatty acid desaturases, referred to as TsD6D-1 and TsD6D-2, are shown in SEQ ID NO: 1 and SEQ ID NO: 3, respectively. The corresponding amino acid sequences for TsD6D-1 and TsD6D-2 are shown in SEQ ID NO:2 and SEQ ID NO:4, respectively. Both sequences encode a potential polypeptide of 510 amino acids.

Alignment of the two *T. suecica* amino acid sequences with Δ6 desaturases from *Isochysis galbana* and *Mortierella alpina* shows extensive diversity across the entire protein with regions of high homology surrounding the conserved histidine boxes (FIG. 1). *I. galbana* and *T. suecica* are marine algae and *M. alpina* is an oleaginous fungus that accumulates high levels of arachidonic acid. The percent identities for these amino acid sequences are shown in Table 1.

TABLE 1

Pair-wise alignment percentage identities for deduced amino acid sequences of D6 desaturases.

| 1 | 2 | 3 | 4 | Organism |
|---|---|---|---|---|
| — | 22 | 22 | 22 | 1 Isochrysis galbana SEQ ID NO: 11 |
|   | — | 37 | 37 | 2 Mortierella alpina SEQ ID NO: 12 |
|   |   | — | 99 | 3 TsD6D-1 SEQ ID NO: 2 |
|   |   |   | — | 4 TsD6D-2 SEQ ID NO: 4 |

I. galbana: Accession AX577009, deduced amino acid from SEQ ID NO: 34, WO02081668.
M. alpina: Accession AAF08685

Example 2

Yeast Transformation and Expression

The pYES2.1/V5-His clones containing TsD6D-1 and TsD6D-2 were introduced into the host strain *Saccharomyces cerevisiae* INVSc1 (auxotrophic for uracil) (Invitrogen) using the PEG/Li Ac protocol as described in the Invitrogen manual for pYES2.1/V5-His-TOPO. Transformants were selected on plates made of SC minimal media minus uracil with 2% glucose. Colonies of transformants were used to inoculate 8 ml of SC minimal media minus uracil and 2% glucose grown overnight at 30° C. For induction, stationary phase yeast cells were pelleted and re-suspended in SC minimal media minus uracil supplemented with 2% galactose and grown for 3 days at 15° C. When exogenous fatty acids were provide to the cultures, 0.01% LA (Δ9, 12-18:2) or 0.01% ALA (Δ9, 12, 15-18:3) was added with the emulsifier 0.1% Tergitol. The cultures were grown for 3 days at 15° C., and subsequently harvested by centrifugation. Cell pellets were washed once with sterile TE buffer pH 7.5, to remove the media, and lyophilized to dryness. The host strain transformed with the vector containing the LacZ gene was used as a negative control in all experiments.

Lipids were extracted from lyophilized yeast pellets by adding 0.1 mL toluene and incubating over-night at room temperature. Extracted lipids were converted to fatty acid methyl esters (FAMEs) in situ by addition of 0.5 mL 0.6N sodium methoxide in methanol and incubating for 45 min at room temperature. The FAMEs were extracted by addition of 0.8 mL 10% (w/v) NaCl and 0.15 mL of heptane. The heptane layer containing FAMEs was removed and used directly for gas chromatography (GC). The FAMEs were identified on a Hewlett-Packard 5890 II Plus GC (Hewlett-Packard, Palo Alto, Calif.) equipped with a flame-ionization detector and a capillary column (omegawax 250; 30 m×0.25 mm i.d.×0.25 μm; Supelco, Bellefonte, Pa.). A 100:1 split ratio was used for injections. The injector was maintained at 250° C. and the flame ionization detector was maintained at 270° C. The column temperature was maintained at 180° C. for 1.5 min following injection, increased to 240° C. at 40° C./min, and held at 245° C. for 3.38 min.

The results shown in Table 2 demonstrate that *T. suecica* clones TsD6D-1 and TsD6D-2 exhibit Δ6 desaturase activity in a yeast expression system. The substrate preference was deduced from a yeast induction assay, whereby yeast cultures induced to express recombinant desaturase are fed LA, ALA, or equal volumes of LA and ALA. The yeast incorporates these fatty acids into their membranes where they become substrates for the recombinant desaturase. The products of LA and ALA Δ6 desaturation are GLA and SDA, respectively. Two individual colonies were selected for each vector. Both *T. suecica* clones demonstrated substrate selectivity for ALA that is 2 to 2.6 fold higher than for LA. The negative control is pYES2.1 vector containing a LacZ insert.

TABLE 2

Delta 6 desaturase activity of *T. suecica* TsD6D-1 and TsD6D-2 in a yeast expression system.

| Construct | FA In Medium | LA | GLA | ALA | SDA | SDA/GLA |
|---|---|---|---|---|---|---|
| neg control | — | 0 | 0 | 0 | 0 | |
| neg control | LA | 13.69 | 0 | 0 | 0 | |
| neg control | ALA | 0 | 0 | 25.02 | 0 | |
| neg control | LA + ALA | 7.96 | 0 | 12.17 | 0 | |
| neg control | — | 0 | 0 | 0 | 0 | |
| neg control | LA | 14.07 | 0 | 0 | 0 | |
| neg control | ALA | 0 | 0 | 26.82 | 0 | |
| neg control | LA + ALA | 8.62 | 0 | 13.44 | 0 | |
| TsD6D-1 | — | 0 | 0 | 0 | 0 | |
| TsD6D-1 | LA | 12.08 | 1.39 | 0 | 0 | |
| TsD6D-1 | ALA | 0 | 0 | 19.87 | 1.27 | |
| TsD6D-1 | LA + ALA | 8.65 | 0.44 | 13.54 | 1.08 | 2.45 |
| TsD6D-1 | — | 0 | 0 | 0 | 0 | |
| TsD6D-1 | LA | 11.61 | 1.2 | 0 | 0 | |
| TsD6D-1 | ALA | 0.53 | 0 | 20.81 | 1.21 | |
| TsD6D-1 | LA + ALA | 8.44 | 0.39 | 13.68 | 1.02 | 2.62 |
| TsD6D-2 | — | 9.43 | 0 | 1.24 | 0 | |
| TsD6D-2 | LA | 16.85 | 0.76 | 0 | 0 | |
| TsD6D-2 | ALA | 0 | 0 | 31.62 | 1.7 | |
| TsD6D-2 | LA + ALA | 5.83 | 0.35 | 8.02 | 0.69 | 1.97 |
| TsD6D-2 | — | 0 | 0 | 0 | 0 | |
| TsD6D-2 | LA | 9.07 | 0.61 | 0 | 0 | |
| TsD6D-2 | ALA | 0 | 0 | 25.78 | 1.54 | |
| TsD6D-2 | LA + ALA | 9.43 | 0.5 | 15.15 | 1.23 | 2.46 |

Example 3

Expression of *Tetraselmis suecica* Δ6-desaturase in Soybean

Figure 2:
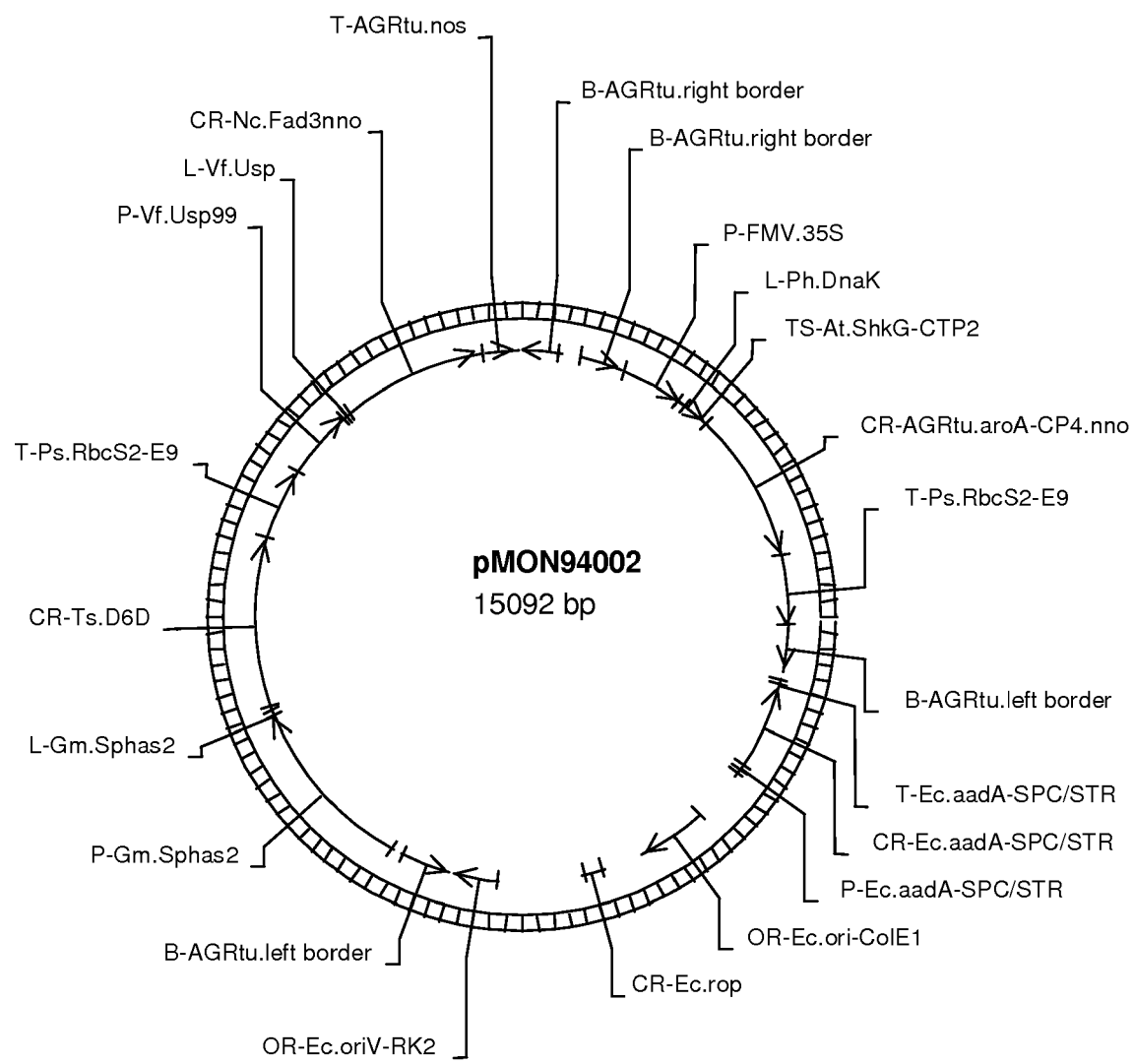
FIG. 2 shows a map of vector pMON94002.

The activity of the *T. suecica* Δ6-desaturase was evaluated in soybean seed by combining it with a dicot codon-enhanced Δ15-desaturase from *Neurospora crassa* (NcFad3nno) (SEQ ID NO: 13) to give pMON94002 (FIG. 2). The vector pMON94002 was constructed in 3 steps. First, the restriction sites, SalI and Sse8387 I were added to the ends of the TsD6D-1 coding sequence (CDS) by PCR amplification from pMON67034 (TsD6D-1 in pYES2.1) using the oligonucleotides TsD6D-F3: 5'-GTCGACAAA-CAATGGGCAGGGGTGGGTTTA-3' (SEQ ID NO:14), and TsD6D-R3: 5'-CCTGCAGGCTAAGCAAGTGCCGCGAT-GTC-3' (SEQ ID NO: 15) to give pMON67051. The TsD6D-1 CDS was next placed behind the seed-specific 7Sα promoter by digesting pMON67051 with SalI and Sse83871 and ligating the resulting fragment into XhoI/Sse8387I-digested pMON67052 to give pMON67053. The resulting 7Sα::TsD6D-1::E9 expression cassette was moved into a plant binary vector containing the NcFad3nno driven by the seed-specific promoter, USP99. This was accomplished by digesting the vector pMON67053 with NotI and then ligating the resulting fragment into partially NotI-digested pMON67046 (vector containing USP99::NcFAD3nno::nos) to give pMON94002.

Transformed explants containing pMON94002, were obtained via *Agrobacterium tumefaciens*-mediated transformation. Plants were regenerated from transformed tissue. The greenhouse-grown plants were then analyzed for oil composition. The effect of expression of the TsD6D-1 coding sequence in conjunction with the NcFad3nno was measured by determining the fatty acid composition of mature seed by gas chromatography of lipid methyl ester derivatives (PCT US03/16144, filed May 21, 2003, the entire disclosure of which is specifically incorporated herein by reference). The levels of OA (oleic acid), LA (linoleic acid), GLA (γ-linolenic acid), ALA (α-linolenic acid) and SDA (stearidonic acid) are expressed as a percentage of the total weight of measured fatty acids and are shown in Table 3. The non-transgenic line A3525 is included as a negative control. Values are expressed as an average of non-nulls from as many as 6 individual R1 seeds.

TABLE 3

Relative Area Percent Results from single R1 seed of soy transformed with pMON94002.

| Pedigree | Gen | Fatty Acid (percent wt) | | | | | |
|---|---|---|---|---|---|---|---|
| | | Oleic | LA | ALA | GLA | SDA | GLA/SDA |
| A3525 | — | 17.44 | 56.1 | 9.1 | — | — | — |
| GM_A74156 | R1 | 15.5 | 47.7 | 16.1 | 3.1 | 0.4 | 7.2 |
| GM_A74004 | R1 | 14.4 | 37.2 | 12.4 | 13.7 | 4.9 | 2.8 |
| GM_A73961 | R1 | 15.8 | 38.6 | 7.0 | 19.2 | 1.5 | 13.0 |
| GM_A73654 | R1 | 14.5 | 28.1 | 5.7 | 27.4 | 4.6 | 5.9 |
| GM_A73962 | R1 | 14.0 | 25.7 | 6.4 | 28.4 | 4.9 | 5.8 |
| GM_A73657 | R1 | 13.5 | 17.3 | 8.7 | 31.8 | 9.2 | 3.5 |
| GM_A74165 | R1 | 17.9 | 20.3 | 4.7 | 33.8 | 3.9 | 8.6 |
| GM_A74162 | R1 | 15.2 | 10.9 | 5.1 | 35.3 | 5.3 | 6.7 |
| GM_A73612. | R1 | 22.6 | 8.1 | 3.1 | 38.1 | 4.3 | 8.8 |
| GM_A73597 | R1 | 18.4 | 6.7 | 3.7 | 39.3 | 6.2 | 6.3 |
| GM_A74496 | R1 | 18.5 | 10.6 | 4.3 | 39.4 | 6.5 | 6.0 |
| GM_A73977 | R1 | 15.6 | 10.6 | 4.9 | 41.1 | 7.9 | 5.2 |
| GM_A73611 | R1 | 18.4 | 12.2 | 3.9 | 41.4 | 4.7 | 8.9 |
| GM_A74014 | R1 | 16.3 | 11.0 | 3.9 | 41.9 | 5.5 | 7.6 |
| GM_A74462 | R1 | 15.4 | 10.1 | 4.8 | 42.3 | 7.0 | 6.0 |
| GM_A74410 | R1 | 15.7 | 8.1 | 4.0 | 42.6 | 7.2 | 6.0 |
| GM_A73997 | R1 | 13.0 | 13.6 | 4.8 | 42.8 | 6.0 | 7.1 |
| GM_A73590 | R1 | 14.8 | 8.4 | 4.3 | 42.8 | 8.0 | 5.3 |
| GM_A73633 | R1 | 18.3 | 9.3 | 3.4 | 43.3 | 4.8 | 9.1 |
| GM_A73645 | R1 | 14.4 | 8.0 | 4.5 | 43.4 | 8.0 | 5.4 |
| GM_A74474 | R1 | 15.1 | 11.4 | 3.9 | 43.5 | 5.6 | 7.8 |
| GM_A74440 | R1 | 15.5 | 7.7 | 4.4 | 43.8 | 7.6 | 5.7 |
| GM_A74155 | R1 | 12.5 | 8.8 | 4.3 | 43.9 | 8.8 | 5.0 |
| GM_A73603 | R1 | 15.1 | 8.1 | 4.5 | 44.0 | 7.3 | 6.0 |
| GM_A74170 | R1 | 14.5 | 13.6 | 3.6 | 44.1 | 3.7 | 11.8 |
| GM_A73675 | R1 | 15.4 | 12.8 | 3.9 | 44.4 | 4.2 | 10.5 |
| GM_A74016 | R1 | 14.0 | 10.7 | 4.1 | 44.6 | 6.1 | 7.3 |
| GM_A73963 | R1 | 11.8 | 8.0 | 4.2 | 44.9 | 9.0 | 5.0 |
| GM_A73617 | R1 | 15.6 | 7.4 | 3.7 | 45.0 | 6.8 | 6.6 |
| GM_A74263 | R1 | 13.3 | 9.4 | 4.6 | 45.0 | 8.2 | 5.5 |
| GM_A74511 | R1 | 12.6 | 7.0 | 4.1 | 45.2 | 9.3 | 4.9 |
| GM_A74422 | R1 | 12.0 | 8.1 | 4.7 | 45.6 | 9.8 | 4.7 |
| GM_A74176 | R1 | 13.8 | 8.6 | 4.2 | 45.7 | 7.6 | 6.0 |
| GM_A73598 | R1 | 14.6 | 8.8 | 3.6 | 45.8 | 5.9 | 7.8 |
| GM_A74463 | R1 | 15.3 | 9.3 | 3.9 | 45.9 | 5.3 | 8.7 |
| GM_A74259 | R1 | 13.5 | 12.4 | 4.2 | 46.1 | 5.8 | 7.9 |
| GM_A74166 | R1 | 14.0 | 10.3 | 3.8 | 46.1 | 5.5 | 8.4 |
| GM_A73588 | R1 | 10.6 | 10.3 | 4.6 | 46.3 | 7.6 | 6.1 |
| GM_A74160 | R1 | 16.9 | 10.1 | 2.8 | 46.4 | 2.5 | 18.3 |
| GM_A73971 | R1 | 15.5 | 10.4 | 2.9 | 47.0 | 3.1 | 15.0 |
| GM_A74451 | R1 | 12.7 | 10.5 | 3.7 | 47.9 | 6.0 | 7.9 |
| GM_A73981 | R1 | 12.9 | 7.2 | 2.8 | 50.3 | 5.3 | 9.5 |

All of the pMON94002 transgenic events in Table 3 accumulate measurable amounts of GLA and SDA. In all cases, the levels of GLA were greater than those of SDA, with GLA values ranging from 3.1% to 50.3% and SDA values ranging from 0.4% to 9.8%. The highest single seed value for GLA was observed from event GM_A73981, which contained 50.3% GLA and 5.3% SDA. Event GM_A74160 has the highest GLA/SDA ratio of 18.3. Of the 41 events shown above, 31 had GLA values >40% in at least three out of four seeds. As GLA values increase, the levels of LA decrease significantly with values starting at 56% and going as low as 6.7%. OA and ALA values also decreased with increasing PUFA but not to the same extent as the LA.

Example 4

Activity of the *Tetraselmis suecica* Δ6-desaturase in Canola and *Arabidopsis*

Figure 3:
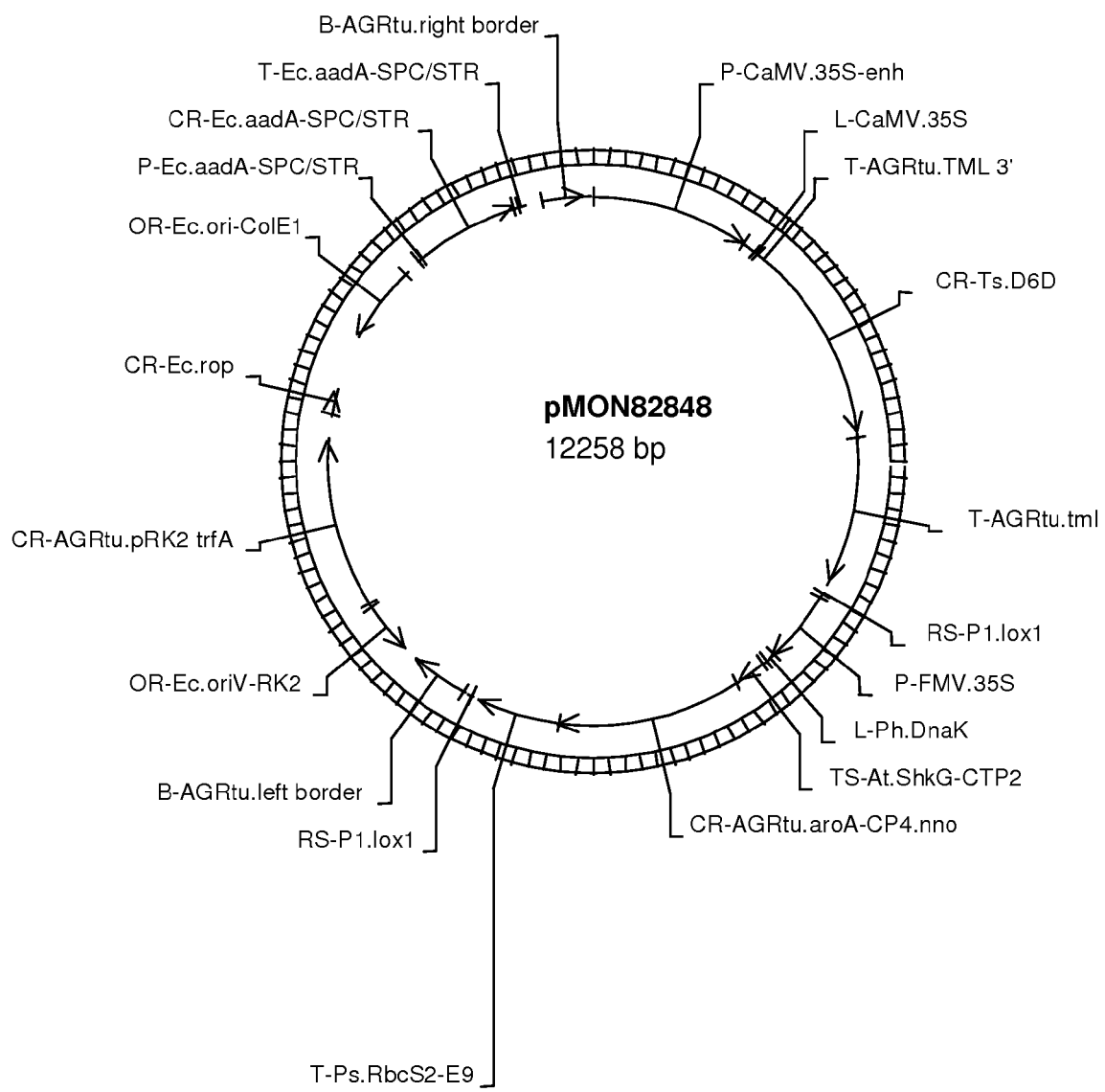
FIG. 3 shows a map of vector pMON82848.
Figure 4:
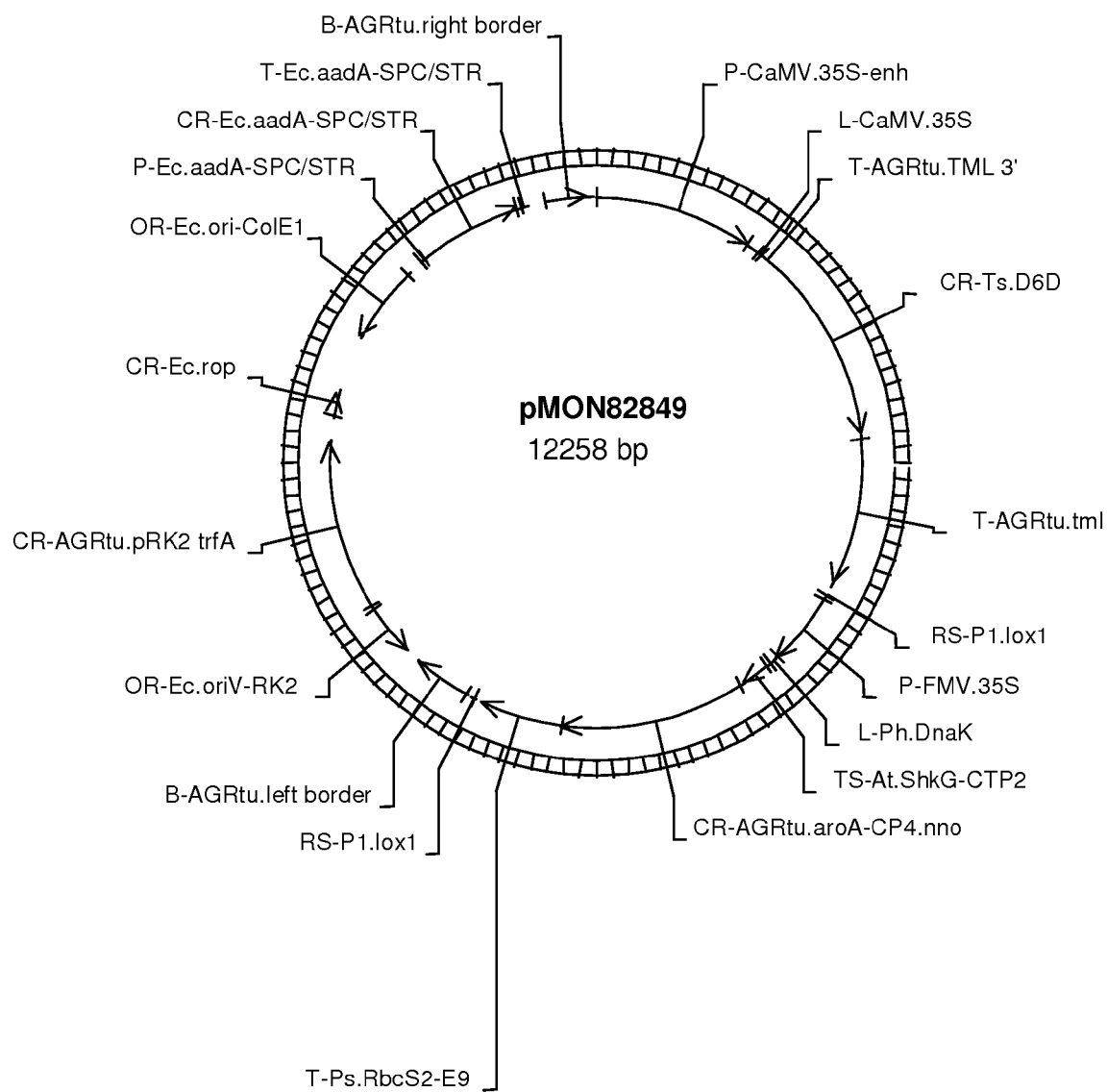
FIG. 4 shows a map of vector pMON82849.

The activity of the *Tetraselmis suecica* Δ6-desaturase was evaluated by transforming Arabidopsis and canola with pMON82848 (TsD6D-1, FIG. 3) and pMON82849 (TsD6D-2, FIG. 4). The native *T. suecica* TsD6D-1 and -2 genes are both driven by a 35S constitutive promoter.

pMON82848 was constructed in 2 steps. First, a consensus dicot Kozak sequence was added to the TsD6D coding sequence by PCR from pMON67034 using the primers TsD6D-F2: 5'-AAAAATGGGCAGGGGTGGGTTTACT-3' (SEQ ID NO:16) and TsD6D-R1: 5'-CTAAGCAAGTGC-CGCGATGTCCG-3' (SEQ ID NO:10) and then ligating the resulting fragment into pCR2.1-TOPO (Invitrogen) to give pMON82833. The vector pMON82833 was then digested with XhoI and SacI and the resulting fragment was ligated into SalI/SacI-digested pMON73273 to give pMON82848. The pMON82849 binary vector was constructed in a similar fashion using the TsD6D-2 variant.

Transformed explants containing pMON82848 and pMON82849 were obtained via *Agrobacterium tumefaciens*-mediated transformation. Plants were regenerated from transformed tissue. The greenhouse-grown plants were then analyzed for oil composition. The fatty acid composition of lyophilized leaves was determined by GC analysis of methyl ester-derived lipids as done above for soybean transformants and are shown in Tables 4 and 5. The levels of OA, LA, GLA, ALA, and SDA are expressed as a percentage of the total weight of measured fatty acids.

The GC analysis of canola leaf from plants transformed with pMON82848 yielded 33 events with GLA levels ranging from 0.7% to 21.5% and SDA levels ranging from 0.5% to 12.9%, respectively. The GLA values are consistently greater than the SDA values giving GLA/SDA ratios of 1.1 to 2.2. The non-transgenic Ebony line is included as a negative control showing high levels of ALA at 54.6%, lower levels of LA at 13.5%, and no measurable amounts of GLA and SDA. Event BN__13396 has the highest level of GLA at 21.5% with LA at 6.6%.

Event BN_G13295 contained 12.9% SDA, which is the highest value observed for this set of canola plants. Oleic acid showed a slight increase from the Ebony control of 1.3% to a high of 3.6% in event BN_G13299. ALA was negatively affected starting at 54.6% in the Ebony control and decreasing to a low of 22.2% in event BN_G13296.

TABLE 4

Relative Area Percent Results from R1 leaves of Canola transformed with pMON82848

| Event | Gen | Fatty Acid (percent wt) | | | | | |
|---|---|---|---|---|---|---|---|
| | | Oleic | LA | GLA | ALA | SDA | GLA/SDA |
| EBONY | VARIETY | 1.4 | 14.3 | 0.0 | 54.2 | 0.0 | — |
| BN_G13292 | R0 | 1.9 | 16.8 | 0.7 | 49.5 | 0.5 | 1.4 |
| BN_G13286 | R0 | 1.9 | 16.1 | 2.1 | 47.6 | 1.9 | 1.1 |
| BN_G13320 | R0 | 1.7 | 11.2 | 7.2 | 40.8 | 5.3 | 1.3 |
| BN_G9283 | R0 | 1.0 | 6.7 | 9.4 | 32.1 | 8.1 | 1.2 |
| BN_G9282 | R0 | 0.9 | 6.0 | 10.1 | 30.6 | 7.8 | 1.3 |
| BN_G13336 | R0 | 2.3 | 14.3 | 10.5 | 34.0 | 6.6 | 1.6 |
| BN_G9281 | R0 | 1.1 | 6.1 | 10.9 | 28.9 | 8.7 | 1.2 |

TABLE 4-continued

Relative Area Percent Results from R1 leaves of Canola transformed with pMON82848

| | | Fatty Acid (percent wt) | | | | | |
|---|---|---|---|---|---|---|---|
| Event | Gen | Oleic | LA | GLA | ALA | SDA | GLA/SDA |
| BN_G13299 | R0 | 3.6 | 11.0 | 12.7 | 30.0 | 9.0 | 1.4 |
| BN_G13367 | R0 | 2.3 | 8.1 | 14.5 | 30.1 | 9.8 | 1.5 |
| BN_G13351 | R0 | 2.4 | 7.4 | 14.7 | 29.8 | 10.8 | 1.4 |
| BN_G13297 | R0 | 2.8 | 7.9 | 14.9 | 26.6 | 12.0 | 1.2 |
| BN_G13289 | R0 | 2.5 | 8.8 | 15.2 | 29.0 | 9.9 | 1.5 |
| BN_G13339 | R0 | 2.7 | 8.0 | 15.6 | 26.7 | 10.0 | 1.6 |
| BN_G13291 | R0 | 2.0 | 6.5 | 16.2 | 29.1 | 10.3 | 1.6 |
| BN_G13337 | R0 | 2.4 | 9.0 | 16.2 | 27.9 | 10.1 | 1.6 |
| BN_G13369 | R0 | 2.8 | 8.1 | 16.4 | 27.4 | 9.3 | 1.8 |
| BN_G13334 | R0 | 2.0 | 8.9 | 16.5 | 29.0 | 9.6 | 1.7 |
| BN_G13295 | R0 | 2.8 | 6.5 | 16.6 | 24.1 | 12.9 | 1.3 |
| BN_G13346 | R0 | 2.6 | 9.3 | 16.7 | 26.6 | 9.3 | 1.8 |
| BN_G13298 | R0 | 2.7 | 9.0 | 16.8 | 27.9 | 9.6 | 1.7 |
| BN_G13342 | R0 | 3.4 | 11.5 | 17.0 | 26.3 | 9.1 | 1.9 |
| BN_G13327 | R0 | 2.2 | 9.3 | 17.0 | 28.2 | 9.2 | 1.8 |
| BN_G13344 | R0 | 2.7 | 7.6 | 17.2 | 26.6 | 9.8 | 1.8 |
| BN_G13294 | R0 | 2.5 | 5.9 | 17.4 | 27.5 | 9.9 | 1.8 |
| BN_G13324 | R0 | 1.4 | 7.0 | 17.5 | 27.8 | 11.3 | 1.6 |
| BN_G13341 | R0 | 2.6 | 8.9 | 18.3 | 26.0 | 9.4 | 1.9 |
| BN_G13332 | R0 | 2.7 | 8.1 | 18.8 | 24.7 | 10.0 | 1.9 |
| BN_G13288 | R0 | 2.5 | 7.4 | 18.8 | 25.5 | 9.9 | 1.9 |
| BN_G13296 | R0 | 3.0 | 7.2 | 20.0 | 22.2 | 11.7 | 1.7 |
| BN_G13340 | R0 | 2.4 | 9.0 | 20.1 | 25.5 | 9.6 | 2.1 |
| BN_G13383 | R0 | 2.5 | 6.1 | 20.5 | 23.5 | 10.0 | 2.1 |
| BN_G13347 | R0 | 2.1 | 7.4 | 20.5 | 25.0 | 10.1 | 2.0 |
| BN_G13396 | R0 | 2.3 | 6.6 | 21.5 | 24.0 | 9.9 | 2.2 |

The GC results for 31 pMON82849 Canola events are shown in Table 5. The pattern of more GLA than SDA is consistent with that observed for pMON82848 plants with ratios of GLA/SDA ranging form 1.0 to 2.3. Event BN_G13422 has the highest level of GLA at 21.9%, which is very similar to the highest pMON82848 value of 21.5% (event BN_G13396).

TABLE 5

Relative Area Percent Results from R1 leaves of Canola transformed with pMON82849

| | | Fatty Acid (percent wt) | | | | | |
|---|---|---|---|---|---|---|---|
| Event | Gen | Oleic | LA | GLA | ALA | SDA | GLA/SDA |
| BN_G9624 | R0 | 1.4 | 13.2 | 3.0 | 45.4 | 2.5 | 1.2 |
| BN_G13441 | R0 | 3.0 | 15.5 | 5.6 | 39.9 | 5.3 | 1.1 |
| BN_G9307 | R0 | 0.6 | 5.0 | 9.9 | 32.7 | 9.5 | 1.0 |
| BN_G13425 | R0 | 2.3 | 9.6 | 11.6 | 32.4 | 10.0 | 1.2 |
| BN_G13460 | R0 | 3.2 | 13.2 | 11.7 | 32.3 | 7.6 | 1.5 |
| BN_G13309 | R0 | 2.1 | 8.3 | 11.8 | 30.9 | 11.3 | 1.0 |
| BN_G13440 | R0 | 2.9 | 13.8 | 12.1 | 31.9 | 8.0 | 1.5 |
| BN_G9364 | R0 | 1.0 | 4.9 | 13.5 | 29.0 | 8.6 | 1.6 |
| BN_G13448 | R0 | 2.5 | 7.7 | 14.6 | 28.0 | 11.9 | 1.2 |
| BN_G13433 | R0 | 2.8 | 11.5 | 14.6 | 29.1 | 9.3 | 1.6 |
| BN_G13313 | R0 | 2.1 | 6.4 | 15.3 | 28.3 | 11.0 | 1.4 |
| BN_G13305 | R0 | 2.5 | 6.1 | 15.7 | 25.2 | 12.2 | 1.3 |
| BN_G13317 | R0 | 2.6 | 6.3 | 16.2 | 27.6 | 11.4 | 1.4 |
| BN_G13489 | R0 | 3.6 | 7.8 | 16.6 | 24.4 | 13.4 | 1.2 |
| BN_G13436 | R0 | 3.2 | 9.9 | 16.7 | 26.9 | 9.7 | 1.7 |
| BN_G13314 | R0 | 3.1 | 7.4 | 16.8 | 22.8 | 12.3 | 1.4 |
| BN_G13319 | R0 | 2.7 | 7.2 | 17.1 | 26.0 | 10.8 | 1.6 |
| BN_G13431 | R0 | 1.8 | 7.0 | 17.2 | 29.5 | 9.2 | 1.9 |
| BN_G13302 | R0 | 2.5 | 7.3 | 17.9 | 24.0 | 12.6 | 1.4 |
| BN_G13308 | R0 | 2.9 | 10.3 | 17.9 | 24.4 | 10.2 | 1.7 |
| BN_G13315 | R0 | 1.5 | 6.5 | 18.1 | 25.1 | 12.8 | 1.4 |
| BN_G13434 | R0 | 2.7 | 9.8 | 18.2 | 25.4 | 9.4 | 1.9 |
| BN_G13300 | R0 | 3.0 | 8.5 | 18.6 | 23.0 | 11.4 | 1.6 |
| BN_G13310 | R0 | 1.9 | 6.6 | 18.8 | 25.9 | 10.7 | 1.8 |
| BN_G13311 | R0 | 3.0 | 7.5 | 19.3 | 23.8 | 10.5 | 1.8 |
| BN_G13306 | R0 | 2.0 | 7.5 | 19.4 | 21.6 | 13.2 | 1.5 |

TABLE 5-continued

Relative Area Percent Results from R1 leaves of Canola transformed with pMON82849

| | | Fatty Acid (percent wt) | | | | | |
|---|---|---|---|---|---|---|---|
| Event | Gen | Oleic | LA | GLA | ALA | SDA | GLA/SDA |
| BN_G13316 | R0 | 2.6 | 6.1 | 20.1 | 23.9 | 11.1 | 1.8 |
| BN_G13318 | R0 | 2.4 | 6.7 | 20.9 | 23.0 | 11.4 | 1.8 |
| BN_G13428 | R0 | 2.6 | 7.3 | 21.3 | 25.8 | 8.9 | 2.4 |
| BN_G13304 | R0 | 2.1 | 6.8 | 21.6 | 22.0 | 11.0 | 2.0 |
| BN_G13422 | R0 | 2.5 | 6.4 | 21.9 | 23.7 | 9.7 | 2.3 |

The fatty acid composition of mature seed collected from the same pMON82848 and pMON82849 events was determined by GC analysis of methyl ester derived lipids as done above for transgenic soybean and are shown in Table 6 and 7. The levels of OA, LA, GLA, ALA, and SDA are expressed as a percentage of the total weight of measured fatty acids.

The GC analysis of canola seed from plants transformed with pMON82848 yielded 32 events with GLA and SDA levels ranging from 1.4% to 5.9% and 0.0% to 1.5%, respectively (weight %, 100 seed pool). The GLA values are consistently greater than the SDA values giving GLA/SDA ratios of 3.6 to 6.1. At this generation the plants are hemizygous for the transgene and therefore the pooled R1 seed represent a segregating population of homozygotes, hemizygotes and nulls. The non-transgenic Ebony line is included as a negative control with 70.9% Oleic Acid, 15.7% LA, 5.8% ALA, and no measurable amounts of GLA or SDA. Event BN_G13368 has the highest level of GLA at 5.9% with LA at 10.6%, which is down from the nontransgenic level of 15.7%. Events BN_G13295 and BN_G13368 both contained 1.5% SDA, which is the highest value observed for this set of canola plants. OA and ALA were less affected by increasing levels of GLA than LA. Although events BN_G13367 and BN_G13299 had between 1.6% and 2.0% GLA, respectively, neither contained measurable amounts of SDA.

TABLE 6

Average Relative Area Percent Results from 100 single R1 seed of Canola transformed with pMON82848.

| | | Fatty Acid (percent wt) | | | | | |
|---|---|---|---|---|---|---|---|
| Event | Gen | Oleic | LA | GLA | ALA | SDA | GLA/SDA |
| EBONY | VARIETY | 70.9 | 15.7 | 0.0 | 5.8 | 0.0 | NA |
| BN_G13336 | R1 | 67.8 | 17.2 | 1.4 | 6.0 | 0.4 | 3.9 |
| BN_G13342 | R1 | 71.8 | 14.3 | 1.5 | 5.1 | 0.3 | 4.5 |
| BN_G13367 | R1 | 71.3 | 14.0 | 1.6 | 5.1 | 0.0 | NA |
| BN_G13299 | R1 | 69.4 | 15.3 | 2.0 | 5.5 | 0.0 | NA |
| BN_G13297 | R1 | 68.9 | 15.2 | 2.3 | 5.0 | 0.5 | 4.9 |
| BN_G13334 | R1 | 65.5 | 17.5 | 2.4 | 7.0 | 0.6 | 4.0 |
| BN_G13339 | R1 | 67.5 | 16.5 | 2.5 | 5.6 | 0.6 | 4.6 |
| BN_G9283 | R1 | 65.7 | 17.1 | 2.6 | 6.2 | 0.7 | 3.6 |
| BN_G9281 | R1 | 66.7 | 16.6 | 2.6 | 6.4 | 0.7 | 3.9 |
| BN_G13337 | R1 | 70.3 | 14.1 | 2.7 | 5.1 | 0.6 | 4.5 |
| BN_G13286 | R1 | 67.0 | 16.4 | 2.7 | 6.0 | 0.7 | 4.0 |
| BN_G13327 | R1 | 69.7 | 14.3 | 2.8 | 5.2 | 0.6 | 4.5 |
| BN_G13298 | R1 | 68.2 | 15.7 | 2.9 | 5.1 | 0.6 | 5.0 |
| BN_G13346 | R1 | 67.7 | 15.3 | 3.1 | 5.9 | 0.7 | 4.3 |
| BN_G13351 | R1 | 63.9 | 18.2 | 3.2 | 6.7 | 0.7 | 4.3 |
| BN_G13289 | R1 | 66.8 | 15.1 | 3.4 | 4.5 | 0.6 | 6.1 |
| BN_G13296 | R1 | 68.7 | 14.5 | 3.4 | 4.8 | 0.7 | 5.2 |
| BN_G13369 | R1 | 65.1 | 16.3 | 3.5 | 7.1 | 0.9 | 3.9 |
| BN_G13324 | R1 | 66.5 | 16.2 | 3.5 | 5.9 | 0.8 | 4.2 |
| BN_G13291 | R1 | 65.9 | 15.0 | 3.6 | 5.0 | 0.7 | 5.6 |
| BN_G13340 | R1 | 69.3 | 14.4 | 3.8 | 4.3 | 0.8 | 4.9 |
| BN_G13344 | R1 | 67.1 | 15.5 | 4.0 | 5.4 | 0.9 | 4.7 |
| BN_G9282 | R1 | 64.5 | 16.5 | 4.0 | 6.2 | 1.2 | 3.4 |
| BN_G13347 | R1 | 66.5 | 15.8 | 4.1 | 5.1 | 0.8 | 5.2 |
| BN_G13341 | R1 | 66.6 | 15.9 | 4.1 | 5.0 | 0.8 | 5.4 |

TABLE 6-continued

Average Relative Area Percent Results from 100 single
R1 seed of Canola transformed with pMON82848.

| | | Fatty Acid (percent wt) | | | | |
|---|---|---|---|---|---|---|
| Event | Gen | Oleic | LA | GLA | ALA | SDA | GLA/SDA |
| BN_G13396 | R1 | 68.6 | 13.4 | 4.3 | 5.2 | 1.1 | 4.1 |
| BN_G13332 | R1 | 67.2 | 14.9 | 4.7 | 5.0 | 1.0 | 4.7 |
| BN_G13294 | R1 | 63.7 | 17.3 | 4.7 | 5.7 | 1.0 | 4.9 |
| BN_G13288 | R1 | 66.9 | 13.4 | 5.0 | 5.7 | 1.3 | 4.0 |
| BN_G13295 | R1 | 67.9 | 11.0 | 5.1 | 4.3 | 1.5 | 3.3 |
| BN_G13383 | R1 | 65.9 | 14.7 | 5.7 | 4.9 | 1.2 | 4.9 |
| BN_G13368 | R1 | 68.7 | 10.7 | 5.9 | 4.5 | 1.5 | 3.9 |

The GC results for 30 pMON82849 Canola events are shown in Table 7. The pattern of more GLA than SDA is consistent with that observed for pMON82848 plants with ratios of GLA/SDA ranging form 3.1 to 6.0. Event BN_G13316 has the highest level of GLA at 8.3%, which is slightly greater than the highest pMON82848 value of 5.9% (event BN_G13368).

TABLE 7

Average Relative Area Percent Results from 100 single
R1 seed of Canola transformed with pMON82849.

| | | Fatty Acid (percent wt) | | | | |
|---|---|---|---|---|---|---|
| Event | Gen | Oleic | LA | GLA | ALA | SDA | GLA/SDA |
| BN_G9397 | R1 | 59.9 | 19.7 | 1.9 | 9.0 | 0.5 | 4.2 |
| BN_G13313 | R1 | 69.7 | 14.2 | 1.9 | 6.2 | 0.5 | 4.0 |
| BN_G13425 | R1 | 74.3 | 11.1 | 2.0 | 3.7 | 0.5 | 4.1 |
| BN_G13440 | R1 | 72.1 | 13.2 | 2.0 | 4.7 | 0.5 | 3.7 |
| BN_G13433 | R1 | 71.7 | 14.1 | 2.1 | 4.3 | 0.5 | 4.1 |
| BN_G9307 | R1 | 68.1 | 15.4 | 2.1 | 6.1 | 0.6 | 3.3 |
| BN_G13460 | R1 | 68.0 | 15.7 | 2.1 | 6.4 | 0.6 | 3.5 |
| BN_G13302 | R1 | 68.7 | 14.1 | 2.7 | 6.1 | 0.7 | 4.0 |
| BN_G13306 | R1 | 68.8 | 13.4 | 2.9 | 6.3 | 0.8 | 3.7 |
| BN_G13448 | R1 | 68.1 | 15.7 | 3.0 | 5.2 | 0.7 | 4.4 |
| BN_G13431 | R1 | 70.7 | 13.5 | 3.2 | 4.4 | 0.8 | 4.3 |
| BN_G13436 | R1 | 71.3 | 12.8 | 3.3 | 4.4 | 0.7 | 4.9 |
| BN_G13319 | R1 | 68.7 | 14.2 | 3.4 | 5.3 | 0.7 | 4.6 |
| BN_G13311 | R1 | 72.3 | 11.5 | 3.5 | 4.3 | 0.7 | 4.9 |
| BN_G13434 | R1 | 66.5 | 16.2 | 3.6 | 5.6 | 0.8 | 4.5 |
| BN_G13308 | R1 | 69.2 | 12.8 | 3.7 | 3.8 | 0.6 | 6.0 |
| BN_G13309 | R1 | 71.7 | 10.9 | 3.7 | 4.3 | 0.9 | 4.4 |
| BN_G13422 | R1 | 71.5 | 11.1 | 3.8 | 4.4 | 1.2 | 3.2 |
| BN_G13300 | R1 | 67.4 | 14.1 | 4.1 | 5.6 | 1.0 | 4.1 |
| BN_G13310 | R1 | 70.6 | 12.2 | 4.3 | 4.4 | 0.8 | 5.1 |
| BN_G13428 | R1 | 73.6 | 9.2 | 4.4 | 3.8 | 1.1 | 3.9 |
| BN_G13305 | R1 | 65.5 | 14.8 | 4.6 | 6.3 | 1.1 | 4.2 |
| BN_G13314 | R1 | 65.3 | 13.4 | 4.7 | 4.6 | 0.9 | 5.6 |
| BN_G13489 | R1 | 63.6 | 16.4 | 4.8 | 6.0 | 1.3 | 3.6 |
| BN_G9364 | R1 | 63.6 | 15.4 | 4.9 | 7.1 | 1.6 | 3.1 |
| BN_G13304 | R1 | 69.8 | 12.4 | 4.9 | 4.1 | 1.0 | 5.2 |
| BN_G13318 | R1 | 70.1 | 9.8 | 6.3 | 3.4 | 1.2 | 5.3 |
| BN_G13317 | R1 | 61.2 | 15.9 | 6.4 | 5.6 | 1.6 | 4.1 |
| BN_G13315 | R1 | 63.2 | 15.1 | 6.6 | 5.5 | 1.5 | 4.4 |
| BN_G13316 | R1 | 61.7 | 13.7 | 8.3 | 4.7 | 1.9 | 4.5 | pMON82848 and pMON82849 were also transformed into Arabidopsis to determine the fatty acid composition in leaf and seed. Transformed explants containing pMON82848 and pMON82849 were obtained via Agrobacterium tumefaciens-mediated transformation. Plants were regenerated from transformed tissue. The greenhouse-grown plants were then analyzed for oil composition The effect of expression of the TsD6D-1 and TsD6D-2 was measured by determining the fatty acid composition of Arabidopsis leaf by gas chromatography of lipid methyl ester derivatives (PCT US03/16144, filed May 21, 2003, the entire disclosure of which is specifically incorporated herein by reference). The Arabidopsis leaves were harvested from young plants and lyophilized to remove all moisture before derivatization. The levels of OA, LA, GLA, ALA, and SDA expressed as a percentage of the total weight of measured fatty acids for 12 pMON82848 events are shown in Table 8. The non-transgenic ecotype Columbia is included as a negative control.

TABLE 8

Relative Area Percent Results from R1 leaves
of Arabidopsis transformed with pMON82848

| | | Fatty Acid (percent wt) | | | | |
|---|---|---|---|---|---|---|
| Event | Gen | Oleic | LA | GLA | ALA | SDA | GLA/SDA |
| Columbia | VARIETY | 1.6 | 13.6 | 0.0 | 53.3 | 0.0 | — |
| AT_G2951 | R1 | 3.1 | 14.4 | 4.0 | 38.9 | 3.0 | 1.4 |
| AT_G2951 | R1 | 9.7 | 15.4 | 5.5 | 29.1 | 3.4 | 1.6 |
| AT_G2951 | R1 | 5.0 | 14.0 | 5.9 | 34.4 | 3.8 | 1.5 |
| AT_G2951 | R1 | 4.3 | 15.5 | 5.9 | 33.4 | 3.9 | 1.5 |
| AT_G2951 | R1 | 5.3 | 14.6 | 5.9 | 34.3 | 4.3 | 1.4 |
| AT_G2951 | R1 | 5.2 | 12.8 | 6.4 | 33.8 | 4.6 | 1.4 |
| AT_G2951 | R1 | 7.5 | 14.9 | 7.3 | 29.4 | 4.3 | 1.7 |
| AT_G2951 | R1 | 6.9 | 14.4 | 7.9 | 29.3 | 4.8 | 1.7 |
| AT_G2951 | R1 | 7.4 | 14.6 | 9.3 | 26.7 | 6.1 | 1.5 |
| AT_G2951 | R1 | 3.7 | 10.8 | 10.4 | 30.7 | 6.8 | 1.5 |
| AT_G2951 | R1 | 5.9 | 12.8 | 10.6 | 27.1 | 6.1 | 1.7 |
| AT_G2951 | R1 | 3.2 | 8.2 | 17.4 | 20.5 | 6.8 | 2.5 |

Table 8 shows that TsD6D is capable of altering the fatty acid composition of Arabidopsis leaf. In all of the events listed above, the values are greater for GLA than SDA, which is similar to the fatty acid pattern observed in transgenic canola and soy seed. The increase in GLA and SDA was at the expense of ALA, which decreases from a non-transgenic value of 62.8% to a low value of 20.5% observed in event AT-G2951. This event had the highest level of GLA (17.4%) and SDA (6.8%). It is interesting to note that even though the level of ALA is 4.5 times greater than LA, the levels of GLA are consistently greater than SDA, again demonstrating the preference that TsD6D has for the omega-6 substrate.

The GC results for 12 pMON82849 Arabidopsis events are shown in Table 9. The pattern of more GLA than SDA is consistent with that observed for pMON82848 plants with ratios of GLA/SDA ranging form 1.4 to 1.9. Event AT_G2952 has the highest level of GLA at 9.9% as compared with the highest GLA value of 17.4% for event AT_G2951 (pMON82848).

TABLE 9

Relative Area Percent Results from R1 leaves
of Arabidopsis transformed with pMON82849.

| | | Fatty Acid (percent wt) | | | | |
|---|---|---|---|---|---|---|
| Event | Gen | Oleic | LA | GLA | ALA | SDA | GLA/SDA |
| AT_G2952 | R1 | 5.5 | 16.1 | 4.6 | 33.5 | 3.0 | 1.6 |
| AT_G2952 | R1 | 4.4 | 14.0 | 5.2 | 36.2 | 3.7 | 1.4 |
| AT_G2952 | R1 | 3.7 | 15.3 | 5.4 | 35.6 | 3.7 | 1.5 |
| AT_G2952 | R1 | 6.2 | 15.7 | 5.4 | 32.4 | 3.4 | 1.6 |
| AT_G2952 | R1 | 4.8 | 20.1 | 6.2 | 31.8 | 3.3 | 1.9 |
| AT_G2952 | R1 | 3.3 | 14.9 | 6.6 | 33.2 | 4.3 | 1.5 |
| AT_G2952 | R1 | 3.7 | 12.1 | 6.8 | 35.3 | 4.7 | 1.4 |
| AT_G2952 | R1 | 3.4 | 15.0 | 7.1 | 32.7 | 4.2 | 1.7 |
| AT_G2952 | R1 | 6.7 | 14.8 | 7.5 | 27.0 | 4.1 | 1.9 |
| AT_G2952 | R1 | 3.5 | 13.8 | 7.9 | 31.0 | 5.4 | 1.5 |
| AT_G2952 | R1 | 2.9 | 13.1 | 8.2 | 33.1 | 5.5 | 1.5 |
| AT_G2952 | R1 | 3.8 | 13.0 | 9.9 | 31.3 | 5.3 | 1.9 |

The fatty acid composition of mature R2 seed from *Arabidopsis* was determined by GC analysis of methyl ester derived lipids as done above for soybean seed. Values for pooled seed from 20 transgenic events from pMON82848 are shown in Table 10 (weight %, 100 seed pool). The GLA and SDA levels ranging from 0.8% to 14.2% and 0.3% to 2.8%, respectively The GLA values are consistently greater than the SDA values. At this R1 generation the plants are hemizygous for the transgene and therefore the pooled R2 seed represent a segregating population of homozygotes, hemizygotes and nulls. The non-transgenic Columbia line is included as a negative control. Event AT_G2914 has the highest level of GLA at 14.3% with SDA at 2.7%.

TABLE 10

Average Relative Area Percent Results from seed of *Arabidopsis* transformed with pMON82848.

| Event | Gen | Fatty Acid (percent wt) | | | | | |
|---|---|---|---|---|---|---|---|
| | | Oleic | LA | GLA | ALA | SDA | GLA/SDA |
| Columbia | VARIETY | 15.4 | 28.3 | 0.0 | 17.9 | 0.0 | NA |
| AT_G2929 | R2 | 17.4 | 26.8 | 0.8 | 16.5 | 0.3 | 2.7 |
| AT_G2926 | R2 | 15.8 | 25.7 | 1.9 | 17.1 | 0.6 | 3.0 |
| AT_G2923 | R2 | 18.3 | 22.5 | 6.0 | 13.2 | 1.7 | 3.5 |
| AT_G2913 | R2 | 17.5 | 22.6 | 6.1 | 13.5 | 1.7 | 3.5 |
| AT_G2917 | R2 | 16.1 | 22.6 | 6.1 | 14.5 | 1.9 | 3.3 |
| AT_G2912 | R2 | 17.0 | 21.8 | 6.6 | 13.7 | 1.7 | 3.9 |
| AT_G2928 | R2 | 15.2 | 22.2 | 6.7 | 15.1 | 1.5 | 4.4 |
| AT_G2915 | R2 | 16.4 | 22.1 | 7.0 | 14.3 | 1.3 | 5.4 |
| AT_G2918 | R2 | 18.0 | 21.5 | 7.5 | 12.7 | 1.6 | 4.6 |
| AT_G2922 | R2 | 16.9 | 20.4 | 8.2 | 12.9 | 2.4 | 3.5 |
| AT_G2916 | R2 | 16.7 | 20.5 | 8.4 | 12.8 | 2.2 | 3.8 |
| AT_G2925 | R2 | 16.8 | 20.3 | 8.8 | 12.6 | 2.0 | 4.3 |
| AT_G2924 | R2 | 16.5 | 20.1 | 9.8 | 11.9 | 2.2 | 4.4 |
| AT_G2911 | R2 | 16.8 | 19.6 | 9.9 | 12.2 | 2.1 | 4.6 |
| AT_G2919 | R2 | 17.1 | 19.8 | 10.2 | 11.0 | 2.3 | 4.4 |
| AT_G2930 | R2 | 15.4 | 19.0 | 11.3 | 12.1 | 2.6 | 4.4 |
| AT_G2927 | R2 | 15.6 | 18.5 | 12.0 | 12.2 | 2.3 | 5.2 |
| AT_G2921 | R2 | 16.6 | 17.1 | 13.2 | 10.7 | 2.9 | 4.6 |
| AT_G2920 | R2 | 16.4 | 16.2 | 14.2 | 10.7 | 2.8 | 5.1 |
| AT_G2914 | R2 | 17.9 | 16.1 | 14.3 | 9.8 | 2.7 | 5.3 |

The GC results for 12 pMON82849 *Arabidopsis* events are shown in Table 11. The pattern of more GLA than SDA is consistent with that observed for pMON82848 plants with ratios of GLA/SDA ranging form 3.2 to 5.1. Event AT_G2947 has the highest level of GLA at 13.3%, which is very similar to the highest GLA value of 14.3% for event AT_G2914 (pMON82848).

TABLE 11

Average Relative Area Percent Results from seed of *Arabidopsis* transformed with pMON82849

| Event | Gen | Fatty Acid (percent wt) | | | | | |
|---|---|---|---|---|---|---|---|
| | | Oleic | LA | GLA | ALA | SDA | GLA/SDA |
| AT_G2946 | R2 | 16.3 | 25.9 | 1.5 | 17.1 | 0.4 | 3.8 |
| AT_G2949 | R2 | 16.4 | 26.2 | 1.9 | 16.6 | 0.4 | 4.4 |
| AT_G2945 | R2 | 17.1 | 23.7 | 5.1 | 13.6 | 1.4 | 3.8 |
| AT_G2932 | R2 | 17.2 | 22.1 | 6.7 | 13.5 | 1.7 | 4.0 |
| AT_G2936 | R2 | 17.9 | 20.3 | 8.7 | 12.1 | 2.1 | 4.2 |
| AT_G2939 | R2 | 18.6 | 18.1 | 10.3 | 11.1 | 2.1 | 4.9 |
| AT_G2944 | R2 | 18.2 | 20.2 | 8.2 | 11.8 | 2.3 | 3.6 |
| AT_G2938 | R2 | 16.3 | 21.2 | 7.5 | 13.5 | 2.3 | 3.3 |
| AT_G2943 | R2 | 16.1 | 21.8 | 7.5 | 13.1 | 2.3 | 3.2 |
| AT_G2931 | R2 | 16.5 | 17.5 | 12.5 | 11.6 | 2.5 | 5.0 |
| AT_G2950 | R2 | 16.3 | 16.7 | 13.3 | 10.9 | 2.6 | 5.1 |
| AT_G2942 | R2 | 16.4 | 19.8 | 9.5 | 12.1 | 2.7 | 3.6 |
| AT_G2935 | R2 | 17.0 | 18.8 | 10.9 | 11.4 | 2.7 | 4.1 |
| AT_G2941 | R2 | 17.1 | 19.0 | 9.3 | 12.1 | 2.7 | 3.4 |
| AT_G2948 | R2 | 16.4 | 18.7 | 10.6 | 11.9 | 2.7 | 3.9 |

TABLE 11-continued

Average Relative Area Percent Results from seed of *Arabidopsis* transformed with pMON82849

| Event | Gen | Fatty Acid (percent wt) | | | | | |
|---|---|---|---|---|---|---|---|
| | | Oleic | LA | GLA | ALA | SDA | GLA/SDA |
| AT_G2940 | R2 | 17.3 | 17.1 | 13.0 | 9.9 | 2.8 | 4.7 |
| AT_G2934 | R2 | 17.4 | 17.0 | 12.5 | 10.6 | 2.9 | 4.3 |
| AT_G2937 | R2 | 15.9 | 17.8 | 12.4 | 11.6 | 3.1 | 3.9 |
| AT_G2947 | R2 | 15.7 | 17.2 | 13.3 | 10.9 | 3.3 | 4.0 |

Example 5

Expression of *Tetraselmis suecica* Δ6 Desaturase in Corn

Figure 5:
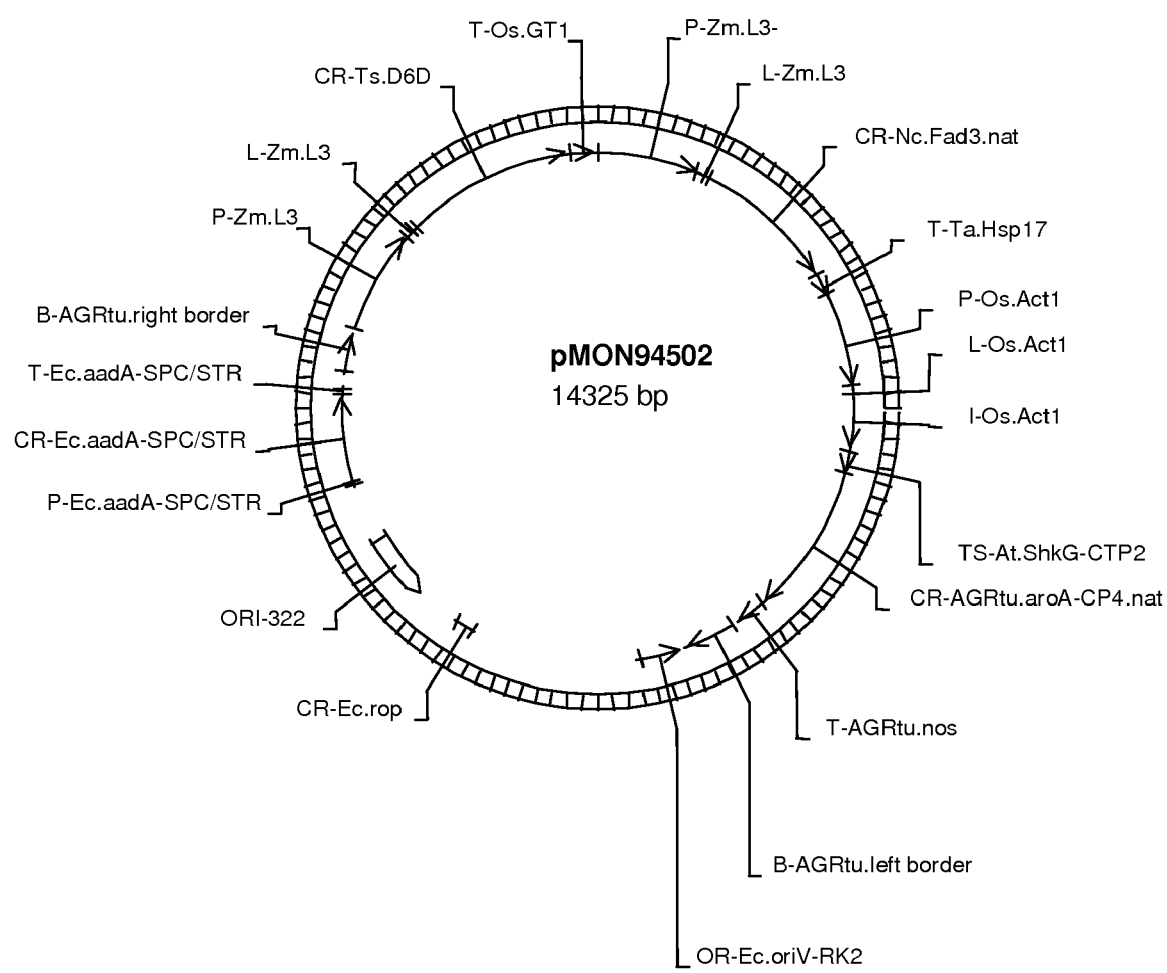
FIG. 5 shows a map of vector pMON94502.

For seed-specific expression of the *Tetraselmis suecica* delta-6 desaturase in corn, TsD6D-1 was cloned under the control of the corn L3-promoter in pMON94502 (FIG. 5) with the rice glutelin 3'-UTR for translation termination. This vector also contained an L3-driven *Neurospora crassa* delta-15 desaturase (SEQ ID NO: 17) expression cassette. The delta-15 expression cassette utilized the wheat HSP17 translation termination sequence as 3'UTR.

Figure 6:
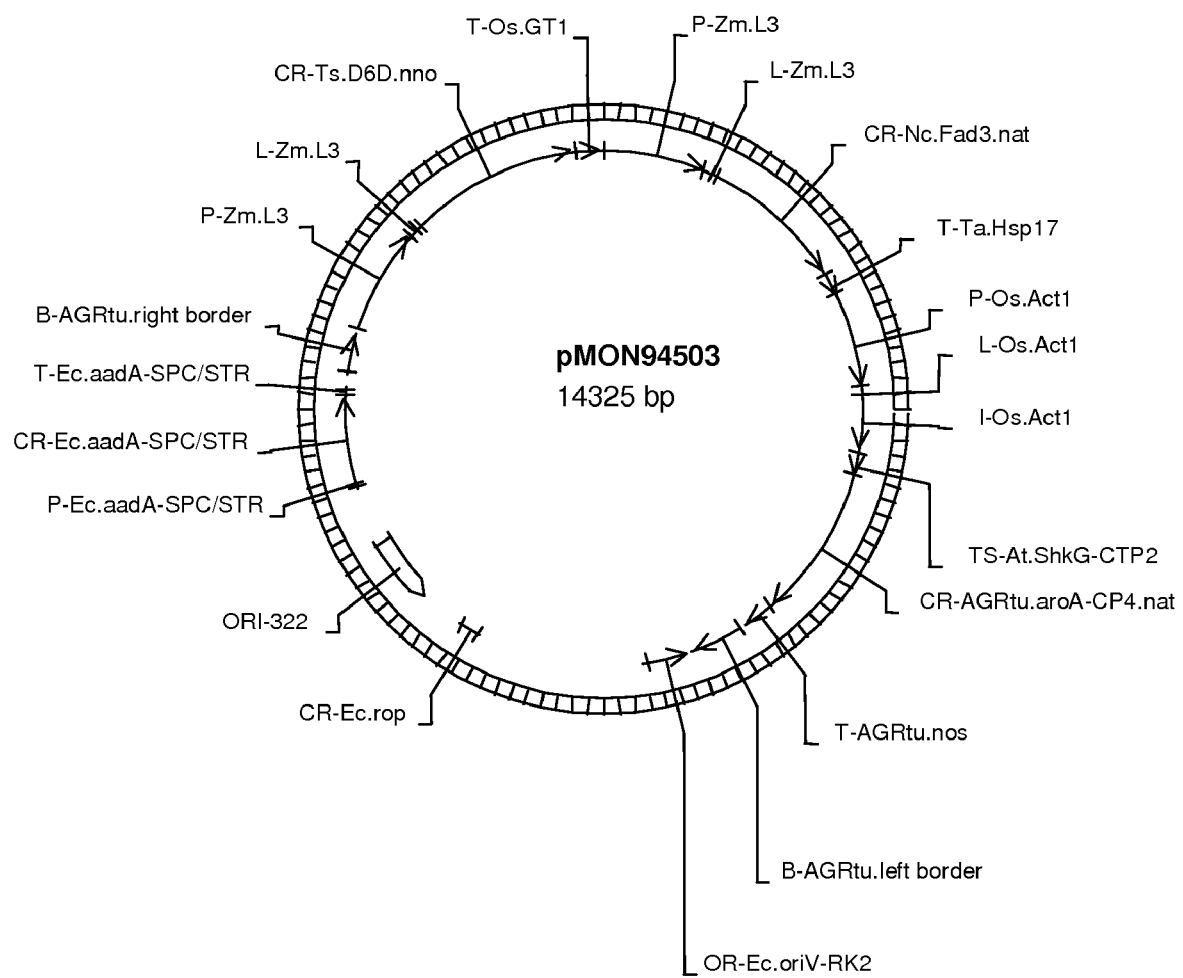
FIG. 6 shows a map of vector pMON94503.

Additionally, a vector containing the TsD6D-1 gene modified for expression in monocotyledonous plants was designed and constructed. It is well known in the art that non-endogenous protein-encoding sequences may not express well in plants (U.S. Pat. No. 5,880,275, herein incorporated by reference). Therefore, using the native TsD6D-1 polypeptide sequence (SEQ ID NO:2), a modified TsD6D-1 protein-encoding polynucleotide sequence was designed and constructed by 1) using a codon usage bias similar to that of highly expressed monocot proteins and by 2) removal of RNA destabilizing elements previously characterized and known to affect mRNA stability in planta (U.S. Pat. No. 5,880,275). The resulting modified TsD6D-1 polynucleotide sequence was designated TsD6Dnno (SEQ ID NO:18) and encodes a polypeptide identical in sequence to the native TsD6D polypeptide (SEQ ID NO:2). TsD6Dnno was cloned into a binary vector that was otherwise identical to pMON94502. The new binary vector was designated pMON94503 (FIG. 6).

Transformed explants containing pMON94502 or pMON94503, respectively, were obtained via *Agrobacterium tumefaciens*-mediated transformation. Plants were regenerated from transformed tissue. The greenhouse-grown plants were then analyzed for oil composition. For every transgenic event that was obtained, ten R1 seed were analyzed for fatty acid composition. The average fatty acid compositions of those seed that exhibited the transgenic trait are shown in Tables 12 and 13. The best performing single seed contained 18.6% SDA, and the best performing seed with regard to GLA-levels contained 30.9% GLA.

TABLE 12

Fatty acid composition of events containing pMON94502.

| Event | % OA | % LA | % ALA | % GLA | % SBA | GLA/SDA |
|---|---|---|---|---|---|---|
| ZM_S137162 | 0.3 | 22.5 | 5.4 | 25.7 | 6.9 | 3.7 |
| ZM_S137159 | 0.9 | 19.5 | 6.7 | 26.1 | 8.7 | 3.0 |
| ZM_S137155 | 1.3 | 15.0 | 7.6 | 25.1 | 12.6 | 2.0 |
| ZM_S137149 | 0.1 | 24.0 | 6.6 | 23.2 | 7.7 | 3.0 |

TABLE 13

Fatty acid composition of events containing pMON94503.

| Event | % Ole | % LA | % ALA | % GLA | % SDA | GLA/SDA |
|---|---|---|---|---|---|---|
| ZM_S139635 | 22.8 | 22.2 | 7.2 | 21.9 | 8.0 | 2.7 |
| ZM_S139623 | 22.7 | 20.3 | 7.2 | 22.2 | 9.1 | 2.4 |
| ZM_S139618 | 22.6 | 33.1 | 19.5 | 4.2 | 3.4 | 1.3 |
| ZM_S139616 | 22.0 | 27.5 | 7.0 | 19.7 | 5.8 | 3.4 |
| ZM_S139613 | 21.9 | 16.4 | 7.6 | 23.8 | 11.8 | 2.0 |
| ZM_S139542 | 22.4 | 23.6 | 7.2 | 21.2 | 7.0 | 3.0 |
| ZM_S139458 | 22.4 | 19.2 | 7.1 | 23.0 | 9.4 | 2.5 |

Example 6

Expression of *Tetraselmis suecica* Δ6 Desaturase in Concert with Other Desaturases For some applications it may be advantageous to optimize GLA biosynthesis or SDA biosynthesis in order to maximize GLA or SDA levels in the oil. Each crop species varies with regard to its seed oil fatty acid composition. As a result the specific strategy to optimize GLA or SDA biosynthesis may vary slightly from crop to crop. To optimize SDA biosynthesis it is advantageous to combine the expression of a delta-6 desaturase with a delta-15 desaturase in order to maximize the substrate pool ALA for the delta-6 desaturase to produce SDA. For example, to obtain an SDA-maximized seed oil, the *Mortierella alpina* delta-15 desaturase and the *T. suecica* delta-6 desaturase are cloned under the control of strong seed-specific promoters utilizing the stronger promoter for the delta-15 desaturase. The construct is transformed into a plant and R1 seed from those plants are analyzed for fatty acid composition.

Some plants such as canola or olives produce seed oils with substantial amounts of monounsaturated fatty acids (oleic acid). In order to convert oleic acid into a substrate for SDA-formation it is desirable to convert OA to LA. This is accomplished by the addition of a delta-12 desaturase to the desaturase combination described above. For example, an *N. crassa* delta-12 desaturase (PCT Publication WO2003099216 (Ursin et al.)), an *N. crassa* delta-15 desaturase, and a *T. suecica* delta-6 desaturase are cloned under the control of seed-specific promoters and transformed into plants. R1 seed of these plants are analyzed for fatty acid composition.

Figure 7:
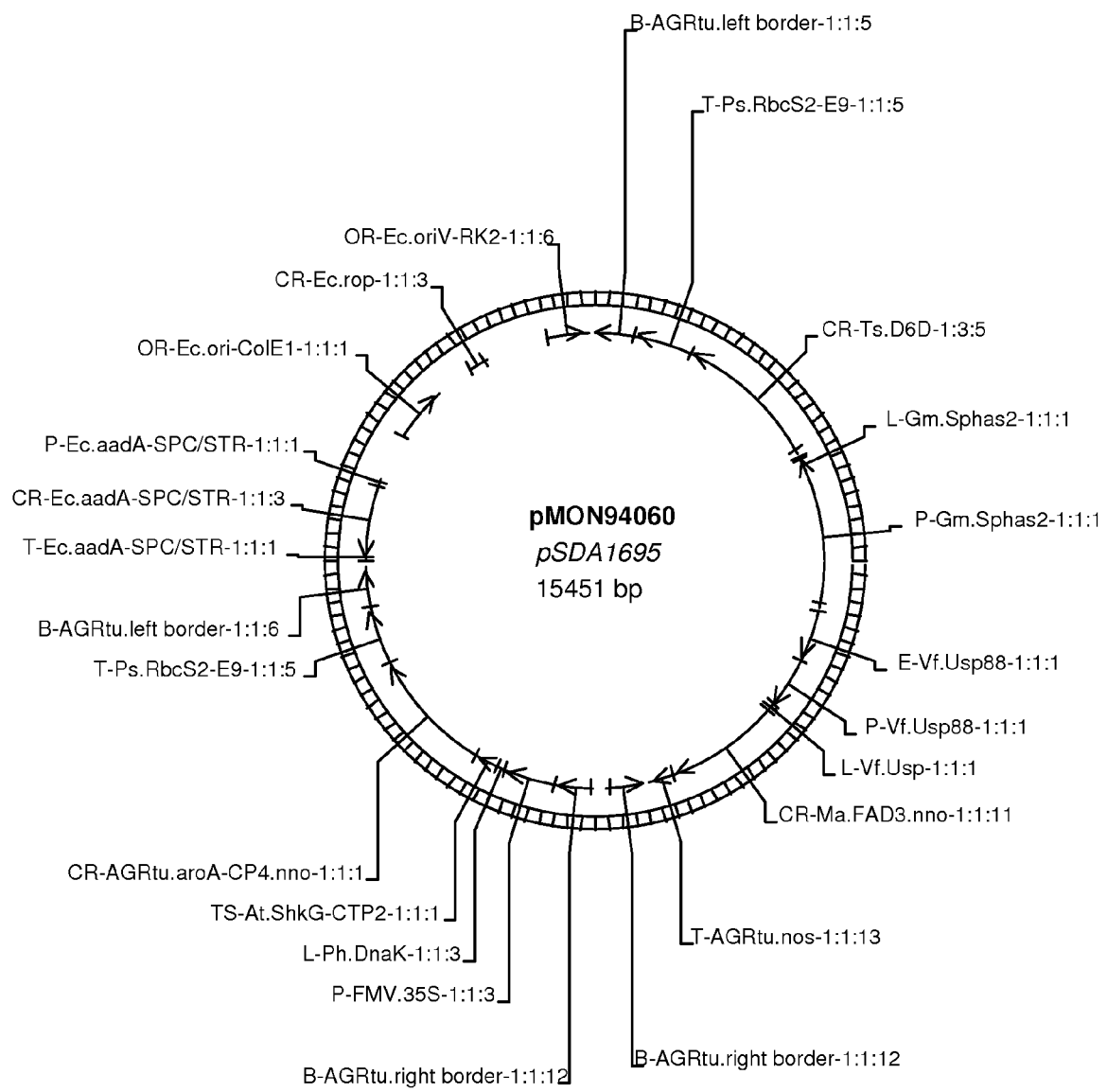
FIG. 7 show a map of vector pMON94060

An example of optimizing the levels of fatty acids in soy is demonstrated. The activity of the *T. suecica* Δ6-desaturase was evaluated in soybean seed by combining it with a dicot codon-enhanced Δ15-desaturase from *M. alpina* (MaFad3nno) (SEQ ID NO: 19) to give pMON94060 (FIG. 7). The vector pMON94060 was constructed in 6 steps. First, the restriction sites, SalI and Sse8387I were added to the ends of the TsD6D-1 coding sequence (CDS) by PCR amplification from pMON67034 (TsD6D-1 in pYES2.1) using the oligonucleotides TsD6D-F3: 5'-GTCGACAAA-CAATGGGCAGGGGTGGGTTTA-3' (SEQ ID NO:14), and TsD6D-R3: 5'-CCTGCAGGCTAAGCAAGTGCCGCGAT-GTC-3' (SEQ ID NO: 15) to give pMON67051. The TsD6D-1 CDS was next placed behind the seed-specific 7Sα promoter by digesting pMON67051 with SalI and Sse8387I and ligating the resulting fragment into XhoI/Sse8387I-digested pMON67052 to give pMON67053. The 7Sα::TsD6D-1::E9 expression cassette was then moved into a plant binary vector, resulting in pMON94055. Restrictions sites, SalI and Sse8387I, were added to the ends of the MaFad3nno CDS by PCR amplification from pMON10351 (MaFad3nno in pYES2.1), using the oligonucleotides MaD15D F1: 5'-GTC-GACAAACAATGGCGCCACCACACGTAGTAGA-3' (SEQ ID NO:20), and MaD15D R1: 5'-CCTGCAGGT-TAGTGCTTGTAGAACACCACATCTCC-3' (SEQ ID NO:21) to give pMON94047. The MaFad3nno CDS was next placed behind the seed-specific eUSP88 promoter by digesting pMON94047 with SalI and Sse8387I and ligating the resulting fragment into XhoI/Sse8387I-digested pMON68776 to give pMON94049. The eUSP88::MaFad3nno::Nos expression cassette was then moved into the pMON94055, resulting in pMON94060.

Transformed explants containing pMON94060, were obtained via *Agrobacterium tumefaciens*-mediated transformation. Plants were regenerated from transformed tissue. The greenhouse-grown plants were then analyzed for oil composition. The effect of expression of the TsD6D-1 coding sequence in conjunction with the MaFad3nno was measured by determining the fatty acid composition of mature seed by gas chromatography of lipid methyl ester derivatives (PCT US03/16144, filed May 21, 2003, the entire disclosure of which is specifically incorporated herein by reference). The levels of OA (oleic acid, 18:9 Δ9), LA (linoleic acid, 18:2 Δ9,12), GLA (γ-linolenic acid, 18:3 Δ6,9,12), ALA (α-linolenic acid, 18:3 Δ9,12,15) and SDA (stearidonic acid, 18:4 Δ6,9,12,15) are expressed as a percentage of the total weight of measured fatty acids and are shown in Table 14. The non-transgenic line A3525 is included as a negative control. Values are expressed as an average of non-nulls from as many as 8 individual R1 seeds.

TABLE 14

Relative Area Percent Results from single R1 seed of soy transformed with pMON94060.

| Event | Oleic | LA | GLA | ALA | SDA | SDA/GLA | GLA/SDA |
|---|---|---|---|---|---|---|---|
| A3525 | 17.4 | 56.1 | | 9.1 | | | |
| GM_A172392 | 22.8 | 13.0 | 36.1 | 2.8 | 2.2 | 0.1 | 16.2 |
| GM_A172882 | 14.9 | 29.6 | 28.8 | 5.9 | 2.5 | 0.1 | 11.3 |
| GM_A172335 | 18.6 | 10.1 | 43.1 | 2.7 | 2.7 | 0.1 | 15.9 |
| GM_A172377 | 21.4 | 8.1 | 38.8 | 3.0 | 2.8 | 0.1 | 13.9 |
| GM_A172386 | 20.9 | 12.7 | 39.0 | 3.7 | 2.9 | 0.1 | 13.7 |
| GM_A172342 | 27.2 | 7.9 | 34.8 | 2.7 | 3.0 | 0.1 | 11.5 |
| GM_A172349 | 19.0 | 8.3 | 40.5 | 2.7 | 3.6 | 0.1 | 11.1 |
| GM_A172423 | 19.4 | 12.6 | 37.0 | 4.1 | 7.4 | 0.2 | 5.0 |
| GM_A172352 | 21.9 | 8.2 | 35.6 | 3.4 | 7.5 | 0.2 | 4.7 |
| GM_A172900 | 19.9 | 27.5 | 1.0 | 20.2 | 12.2 | 12.7 | 0.1 |
| GM_A173156 | 20.2 | 13.0 | 2.0 | 35.4 | 12.9 | 6.3 | 0.2 |
| GM_A172866 | 26.0 | 28.4 | 0.7 | 11.2 | 13.3 | 18.8 | 0.1 |
| GM_A172400 | 20.6 | 6.9 | 29.3 | 3.8 | 13.7 | 0.5 | 2.1 |
| GM_A172390 | 23.0 | 12.4 | 2.9 | 24.9 | 16.1 | 5.5 | 0.2 |
| GM_A172897 | 25.2 | 25.5 | 1.1 | 8.7 | 16.1 | 15.4 | 0.1 |
| GM_A172368 | 38.8 | 1.1 | 0.7 | 7.1 | 24.3 | 34.5 | 0.0 |
| GM_A172343 | 18.6 | 16.2 | 9.4 | 7.1 | 25.1 | 2.7 | 0.4 |
| GM_A172365 | 32.4 | 2.7 | 0.5 | 8.4 | 25.9 | 52.2 | 0.0 |
| GM_A172405 | 30.1 | 2.3 | 2.9 | 8.4 | 27.3 | 9.5 | 0.1 |
| GM_A172384 | 12.2 | 11.8 | 19.5 | 6.9 | 28.3 | 1.4 | 0.7 |
| GM_A172883 | 30.4 | 3.6 | 2.1 | 8.6 | 28.4 | 13.7 | 0.1 |
| GM_A172885 | 22.2 | 10.1 | 3.2 | 9.9 | 30.4 | 9.4 | 0.1 |
| GM_A172411 | 22.9 | 8.9 | 2.0 | 9.6 | 31.2 | 15.5 | 0.1 |
| GM_A172356 | 22.0 | 8.7 | 3.4 | 8.3 | 31.4 | 9.1 | 0.1 |
| GM_A172855 | 23.7 | 6.0 | 5.9 | 10.7 | 31.6 | 5.4 | 0.2 |
| GM_A172393 | 19.1 | 4.9 | 10.3 | 8.5 | 31.7 | 3.1 | 0.3 |
| GM_A172889 | 23.4 | 4.5 | 3.8 | 8.7 | 32.6 | 8.7 | 0.1 |
| GM_A172339 | 20.5 | 4.7 | 3.4 | 13.7 | 33.1 | 9.7 | 0.1 |
| GM_A172849 | 23.2 | 3.7 | 4.2 | 8.9 | 33.7 | 8.0 | 0.1 |
| GM_A173155 | 14.4 | 15.5 | 4.4 | 7.0 | 34.6 | 7.9 | 0.1 |
| GM_A172891 | 15.6 | 15.8 | 5.0 | 8.7 | 34.7 | 6.9 | 0.1 |
| GM_A172357 | 24.4 | 3.8 | 3.6 | 8.6 | 35.0 | 9.7 | 0.1 |
| GM_A172888 | 18.5 | 10.4 | 3.4 | 8.7 | 35.1 | 10.5 | 0.1 |
| GM_A173152 | 14.8 | 15.6 | 5.4 | 9.2 | 35.4 | 6.6 | 0.2 |
| GM_A172862 | 21.3 | 4.9 | 5.2 | 8.8 | 35.7 | 6.9 | 0.1 |

TABLE 14-continued

Relative Area Percent Results from single R1 seed of soy transformed with pMON94060.

| Event | Oleic | LA | GLA | ALA | SDA | SDA/GLA | GLA/SDA |
|---|---|---|---|---|---|---|---|
| GM_A172421 | 21.6 | 5.2 | 6.1 | 8.3 | 36.1 | 5.9 | 0.2 |
| GM_A172370 | 17.0 | 4.7 | 4.5 | 11.9 | 36.7 | 8.1 | 0.1 |
| GM_A172347 | 20.6 | 3.3 | 3.4 | 8.7 | 36.8 | 10.8 | 0.1 |
| GM_A172389 | 18.4 | 5.0 | 6.6 | 8.5 | 37.8 | 5.7 | 0.2 |
| GM_A172838 | 17.6 | 6.3 | 3.2 | 10.9 | 38.1 | 12.1 | 0.1 |
| GM_A172896 | 14.6 | 10.4 | 5.3 | 10.2 | 38.1 | 7.2 | 0.1 |
| GM_A172860 | 16.1 | 10.9 | 4.3 | 8.9 | 38.3 | 8.8 | 0.1 |
| GM_A172363 | 22.3 | 5.2 | 6.8 | 7.4 | 38.5 | 5.6 | 0.2 |
| GM_A172415 | 17.4 | 6.2 | 7.1 | 9.0 | 38.5 | 5.5 | 0.2 |
| GM_A172852 | 17.5 | 8.5 | 3.9 | 8.4 | 38.7 | 10.0 | 0.1 |
| GM_A172847 | 15.0 | 12.5 | 5.4 | 8.9 | 38.8 | 7.2 | 0.1 |
| GM_A172355 | 12.6 | 12.7 | 6.2 | 8.2 | 38.8 | 6.2 | 0.2 |
| GM_A172408 | 16.9 | 6.4 | 7.3 | 8.5 | 39.2 | 5.4 | 0.2 |
| GM_A172371 | 12.5 | 12.2 | 7.0 | 8.0 | 39.4 | 5.7 | 0.2 |
| GM_A172341 | 17.3 | 5.8 | 7.4 | 8.5 | 39.5 | 5.3 | 0.2 |
| GM_A172871 | 16.5 | 9.1 | 3.9 | 8.7 | 40.0 | 10.2 | 0.1 |
| GM_A172337 | 14.5 | 6.9 | 5.9 | 10.0 | 41.0 | 6.9 | 0.1 |
| GM_A172387 | 16.6 | 4.3 | 6.7 | 8.2 | 41.1 | 6.1 | 0.2 |
| GM_A172417 | 16.6 | 5.8 | 4.3 | 8.9 | 41.7 | 9.6 | 0.1 |
| GM_A172361 | 20.9 | 3.2 | 2.2 | 9.2 | 41.8 | 19.2 | 0.1 |
| GM_A172351 | 15.1 | 5.8 | 6.0 | 9.4 | 41.9 | 7.0 | 0.1 |
| GM_A172880 | 18.1 | 4.5 | 4.2 | 7.9 | 42.1 | 10.0 | 0.1 |
| GM_A172419 | 15.0 | 4.3 | 6.3 | 7.7 | 42.1 | 6.7 | 0.2 |
| GM_A172398 | 14.9 | 5.2 | 7.8 | 7.3 | 42.4 | 5.5 | 0.2 |
| GM_A172854 | 15.4 | 3.6 | 3.5 | 12.9 | 42.5 | 12.3 | 0.1 |
| GM_A172843 | 13.5 | 6.7 | 7.9 | 8.0 | 42.6 | 5.4 | 0.2 |
| GM_A172840 | 13.6 | 6.3 | 8.4 | 7.9 | 42.9 | 5.1 | 0.2 |
| GM_A173157 | 12.6 | 6.2 | 9.2 | 8.1 | 43.0 | 4.7 | 0.2 |
| GM_A172345 | 15.2 | 4.1 | 5.6 | 8.0 | 44.0 | 7.8 | 0.1 |
| GM_A172853 | 14.8 | 5.1 | 5.4 | 9.2 | 44.0 | 8.2 | 0.1 |
| GM_A172372 | 14.8 | 5.2 | 6.5 | 7.1 | 44.1 | 6.7 | 0.1 |
| GM_A172358 | 15.9 | 6.8 | 3.3 | 7.6 | 45.0 | 13.5 | 0.1 |
| GM_A172868 | 13.8 | 5.0 | 5.0 | 8.7 | 45.5 | 9.0 | 0.1 |
| GM_A172884 | 14.0 | 4.4 | 4.9 | 7.9 | 46.2 | 9.4 | 0.1 |
| GM_A172879 | 11.9 | 5.9 | 5.0 | 8.8 | 46.6 | 9.3 | 0.1 |
| GM_A172360 | 12.4 | 6.4 | 7.6 | 7.3 | 46.7 | 6.2 | 0.2 |
| GM_A172858 | 13.0 | 4.0 | 5.1 | 8.8 | 46.9 | 9.3 | 0.1 |
| GM_A172873 | 12.7 | 4.3 | 5.3 | 7.9 | 47.5 | 8.9 | 0.1 |

All of the pMON94060 transgenic events in Table 14 accumulate measurable amounts of GLA and SDA. Single seed values of less than 1% were not included in calculating the average for each individual event. For 10 of the events, the levels of GLA are higher than SDA, but for the remaining events the levels of SDA/GLA ranged from 1.6% to 52.2. The highest average value for GLA is 43.1% observed in event GM_A172335, which has only 2.72% SDA. Event GM_A172365 has the highest SDA/GLA ratio of 52.2. Thirty two percent of the events have SDA values grater than 40%. The highest SDA value was 47.5% in event GM_A172873. The levels of LA decreased with increasing levels of SDA and ranged from 1.1% to 29.6%. For 38 of the events, the levels of oleic acid are higher than the 17.4% non-transgenic control value. The highest oleic acid value was 38.8% observed in event GM_A172368. The GLA values ranged from a low of 0.5 in event GM_A172365 to a high of 43.1% in event GM_A172335. The ALA levels in most of the events were close to the original non-transgenic level of 9.1%. Approximately 83.5% or 61 events out of the 73 have between 5.0% and 13.7% ALA.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,518,584; U.S. Pat. No. 4,737,462; U.S. Pat. No. 4,810,648; U.S. Pat. No. 4,826,877; U.S. Pat. No. 4,957,748; U.S. Pat. No. 5,094,945; U.S. Pat. No. 5,100,679; U.S. Pat. No. 5,158,975; U.S. Pat. No. 5,196,525; U.S. Pat. No. 5,219,596; U.S. Pat. No. 5,290,924; U.S. Pat. No. 5,322,783; U.S. Pat. No. 5,359,142; U.S. Pat. No. 5,424,398; U.S. Pat. No. 5,424,412; U.S. Pat. No. 5,500,365; U.S. Pat. No. 5,530,196; U.S. Pat. No. 5,538,880; U.S. Pat. No. 5,550,318; U.S. Pat. No. 5,563,055; U.S. Pat. No. 5,610,042; U.S. Pat. No. 5,627,061; U.S. Pat. No. 5,633,435; U.S. Pat. No. 5,641,876; U.S. Pat. No. 5,880,275; U.S. Pat. No. 5,936,069; U.S. Pat. No. 6,005,076; U.S. Pat. No. 6,040,497; U.S. Pat. No. 6,051,753; U.S. Pat. No. 6,146,669; U.S. Pat. No. 6,156,227; U.S. Pat. No. 6,319,698; U.S. Pat. No. 6,433,252; U.S. Pat. No. 6,451,567; U.S. Patent Publn. 20030093828; U.S. Patent Publn. 20030229918; U.S. Patent Publn. 20040039058

Barany et al., *Int. J. Peptide Protein Res.*, 30:705-739, 1987.
Bauer et al., *Gene*, 37:73, 1985.
Belanger and Kriz, *Genetics*, 129:863-872, 1991.
Bevan et al., *Nucleic Acids Res.*, 11(2):369-385, 1983.
Bodanszky, In: *Principles of Peptide Synthesis*, Springer-Verlag, Heidelberg, 1984.
Bustos et al., *Plant Cell*, 1(9):839-853, 1989
Callis et al., *Genes Dev.*, 1:1183-1200, 1987.
Chen et al., *Proc. Natl. Acad. Sci. USA*, 83: 8560-8564, 1986.
Chu et al., *Scientia Sinica*, 18:659, 1975.
de Deckerer, *Eur. J. Clin. Nutr.*, 52:749, 1998.
DeBlock et al., *EMBO J.*, 6:2513-2519, 1987.
Ebert et al., *Proc. Natl. Acad. Sci. USA*, 84(16):5745-5749, 1987.
Freitag M and Selker E U, *Curr Opin Genet Dev.* 15(2):191-9, 2005.
Gallie et al., *The Plant Cell*, 1:301, 1999.
Hudspeth et al., *Plant Mol. Biol.*, 12:579, 1989.
Ingelbrecht et al., *Plant Cell*, 1(7):671-680, 1989.
James et al., *Semin. Arthritis Rheum.*, 28:85, 2000.
Jones et al., *Plant Cell*, 7(3): 359-371, 1995.
Joshi, *Nucl. Acid Res.*, 15:6643, 1987.
Kridl et al., *Seed Sci. Res.*, 1:209-219, 1991
Lopes et al., *Mol. Gen. Genet.*, 247:603-613, 1995.
Maniatis, et al., Molecular Cloning, A Laboratory Manual, Cold Spring Harbor Press, Cold Spring Harbor, N.Y., 1989.
Maundrell, *J. Biol. Chem.*, 265 (19), 10857-10864, 1990.
Merrifield, *J. Am. Chem. Soc.*, 85:2149-2154, 1963.
Misawa et al, *Plant J.*, 6:481-489, 1994.
Misawa et al., *Plant J.*, 4:833-840, 1993.
Murashige and Skoog, *Physiol. Plant*, 15:473-497, 1962.
Napier et al., *Biochem. J.*, 328, 717-720, 1997.
Napier et al., *Prostaglandins Leukot. Essent. Fatty Acids*, 68 (2), 135-143, 2003.

Naylor et al., *Nature*, 405:1017, 2000.
PCT Appln. PCT US 0306870
PCT Appln. PCT US03/16144
PCT Publn. WO 95/06128
PCT Publn. WO 96/33155
PCT Publn. WO02081668
PCT Publn. WO200250295
PCT Publn. WO2003099216
Prem Das et al., *NAR*, 19(12):3325-3330, 1991.
Recombinant DNA Part D, Methods in Enzymology, Vol. 153, Wu and Grossman (Eds.), Academic Press, 1987.
Sambrook et al., In: *Molecular cloning*, Cold Spring Harbor Laboratory Press, Cold Spring Harbor, N.Y., 2001, 1989

Sathasiivan et al., *Nucl. Acids Res.*, 18:2188-2193, 1990.
Shanklin et al., *Biochemistry*, 33:12787-12794, 1994.
Simopoulos et al., *Am. Coll. Nutr.*, 18:487, 1999.
Sperling and Heinz, *Eur. J. Lipid Sci. Technolo.*, 103, 158-180, 2001.
Stacey et al., *Plant Mol. Biol.*, 31: 1205-1216, 1996.
Turner and Foster, *Mol. Biotechnol.*, 3:225-36, 1995.
Vasil et al., *Plant Physiol.*, 91:1575-1579, 1989.
Walder et al. *Gene*, 42:133, 1986.
West et al., *Mol. Cell Biol.*; 4(11):2467-2478, 1984.
Wohlleben et al., *Gene*, 70:25-37, 1988.

The invention claimed is:

1. An isolated polynucleotide encoding a polypeptide having desaturase activity that desaturates a fatty acid molecule at carbon 6, wherein the polynucleotide is selected from the group consisting of:
   a) a polynucleotide encoding the polypeptide sequence of SEQ ID NO:2 or SEQ ID NO:4;
   b) a polynucleotide comprising the nucleic acid sequence of SEQ ID NO:1;
   c) a polynucleotide hybridizing to SEQ ID NO:1 or a full length complement thereof, under conditions of 5×SSC, 50% formamide and 42° C.; and
   d) a polynucleotide encoding a polypeptide with at least 85% sequence identity to a polypeptide sequence of SEQ ID NO:2 or SEQ ID NO:4.

2. A DNA construct comprising:
   a) a polynucleotide encoding the polypeptide sequence of SEQ ID NO:2 or SEQ ID NO:4:
   b) a polynucleotide comprising the nucleic acid sequence of SEQ ID NO:1;
   c) a polynucleotide hybridizing to SEQ ID NO:1 or a full length complement thereof, under conditions of 5×SSC, 50% formamide and 42° C.; and
   d) a polynucleotide encoding a polypeptide with at least 85% sequence identity to a polypeptide sequence of SEQ ID NO:2 or SEQ ID NO:4.

3. The DNA construct of claim 2 further comprising a heterologous promoter operably linked to the polynucleotide.

4. The DNA construct of claim 2 further comprising at least one additional polynucleotide encoding a fatty acid desaturase.

5. A host cell transformed with the DNA construct of claim 2.

6. The host cell of claim 5, wherein the host cell is a plant cell.

7. The host cell of claim 5, wherein the host cell is a fungal or bacterial cell.

8. The host cell of claim 5, wherein the host cell exhibits altered fatty acid biosynthesis relative to a cell of the same genotype as said host cell but lacking said DNA construct.

9. The host cell of claim 5, wherein the cell has inherited said DNA construct from a progenitor of the cell.

10. A transgenic plant transformed with the DNA construct of claim 2.

11. The plant of claim 10 wherein the plant is selected from the group consisting of canola, *Brassica campestris*, oilseed rape, rapeseed, soybean, crambe, mustard, castor bean, peanut, sesame, cottonseed, linseed, safflower, oil palm, flax, sunflower, corn, rice, barley, millet, rye, wheat, oat, alfalfa and sorghum.

12. The plant of claim 10, further comprising at least one additional polynucleotide encoding a fatty acid desaturase.

13. A seed of the plant of claim 10, wherein the seed comprises the DNA construct.

14. A method of producing food or feed, comprising the steps of:
   (a) obtaining the transgenic plant according to claim 10 or a part thereof; and
   (b) producing said food or feed.

15. The method of claim 14, wherein the food or feed is oil, silage, meal, grain, starch, flour or protein.

16. A food or feed composition produced by the method of claim 14 and comprising a detectable nucleic acid molecule comprising said DNA construct.

17. A food or feed composition produced by the method of claim 14 wherein the food or feed composition comprises said construct.

18. The isolated polynucleotide according to claim 1, wherein said polynucleotide comprises the nucleic acid sequence of SEQ ID NO:18.

19. The DNA construct according to claim 2, wherein said polynucleotide comprises the nucleic acid sequence of SEQ ID NO:18.

* * * * *